United States Patent [19]

Karanewsky

[11] Patent Number: 5,025,000
[45] Date of Patent: Jun. 18, 1991

[54] PHOSPHORUS-CONTAINING HMG-COA REDUCTASE INHIBITOR COMPOUNDS

[75] Inventor: Donald S. Karanewsky, Robbinsville, N.J.

[73] Assignee: E. R. Squibb & Sons, Inc., Princeton, N.J.

[21] Appl. No.: 487,366

[22] Filed: Mar. 2, 1990

[51] Int. Cl.$^5$ .................. C07D 471/04; A61K 31/435
[52] U.S. Cl. .......................................... 514/80; 546/23
[58] Field of Search .................... 546/22, 23; 514/299, 514/80

[56] References Cited

FOREIGN PATENT DOCUMENTS 8801997 3/1988 PCT Int'l Appl. .................. 548/252
2205838 12/1988 United Kingdom ................ 548/484

*Primary Examiner*—Frederick E. Waddell
*Assistant Examiner*—Zinna Northington-Davis
*Attorney, Agent, or Firm*—Burton Rodney

[57] ABSTRACT

Compounds which are useful as inhibitors of cholesterol biosynthesis and thus as hypocholesterolemic agents are provided which have the structure

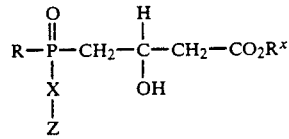

including salts thereof, wherein
R is OH, or lower alkoxy;
$R^x$ is H or alkyl;
X is —$(CH_2)_a$— (where a is 1, 2 or 3), —CH=CH—, or —C≡C—.

New intermediates used in preparing the above compounds, pharmaceutical compositions containing such compounds and a method for using such compounds to inhibit cholesterol biosynthesis are also provided.

14 Claims, No Drawings

PHOSPHORUS-CONTAINING HMG-COA REDUCTASE INHIBITOR COMPOUNDS

FIELD OF THE INVENTION

The present invention relates to new phosphorus-containing compounds which inhibit the activity of 3-hydroxy-3-methylglutaryl-coenzyme A reductase and thus are useful in inhibiting cholesterol biosynthesis, to hypocholesterolemic compositions containing such compounds, to new intermediates formed in the preparation of such compounds and to a method of using such compounds for such purposes.

BACKGROUND OF THE INVENTION

F. M. Singer et al., *Proc. Soc. Exper. Biol. Med.*, 102, 370 (1959) and F. H. Hulcher, *Arch. Biochem. Biophys.*, 146, 422 (1971) disclose that certain mevalonate derivatives inhibit the biosynthesis of cholesterol.

Endo et al in U.S. Pat. Nos. 4,049,495, 4,137,322 and 3,983,140 disclose a fermentation product which is active in the inhibition of cholesterol biosynthesis. This product is called compactin and was reported by Brown et al., (*J. Chem. Soc. Perkin I.* 1165 (1976)) to have a complex mevalonolactone structure.

GB 1,586,152 discloses a group of synthetic compounds of the formula

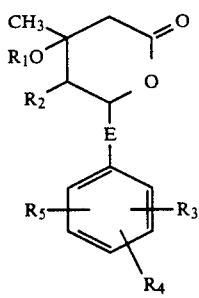

in which E represents a direct bond, a $C_{1-3}$ alkylene bridge or a vinylene bridge and the various R's represent a variety of substituents.

The activity reported in the U.K. patent is less than 1% that of compactin.

U.S. Pat. No. 4,375,475 to Willard et al discloses hypocholesterolemic and hypolipemic compounds having the structure

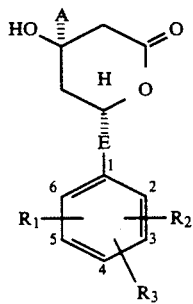

wherein A is H or methyl; E is a direct bond, $-CH_2-$, $-CH_2-CH_2-$, $-CH_2-CH_2-CH_2-$ or $-CH=CH-$; $R_1$, $R_2$ and $R_3$ are each selected from H, halogen, $C_{1-4}$ alkyl, $C_{1-4}$ haloalkyl, phenyl, phenyl substituted by halogen, $C_{1-4}$ alkoxy, $C_{2-8}$ alkanoyloxy, $C_{1-4}$ alkyl, or $C_{1-4}$ haloalkyl, and $OR_4$ in which $R_4$ is H, $C_{2-8}$ alkanoyl, benzoyl, phenyl, halophenyl, phenyl $C_{1-3}$ alkyl, $C_{1-9}$ alkyl, cinnamyl, $C_{1-4}$ haloalkyl, allyl, cycloalkyl-$C_{1-3}$-alkyl, adamantyl-$C_{1-3}$-alkyl, or substituted phenyl $C_{1-3}$-alkyl in each of which the substituents are selected from halogen, $C_{1-4}$ alkoxy, $C_{1-4}$ alkyl, or $C_{1-4}$ haloalkyl; and the corresponding dihydroxy acids resulting from the hydrolytic opening of the lactone ring, and the pharmaceutically acceptable salts of said acids, and the $C_{1-3}$ alkyl and phenyl, dimethylamino or acetylamino substituted $C_{1-3}$-alkyl esters of the dihydroxy acids; all of the compounds being the enantiomers having a 4 R configuration in the tetrahydropyran moiety of the trans racemate shown in the above formula.

WO 84/02131 (PCT/EP83/00308) (based on U.S. application Ser. No. 443,668, filed Nov. 22, 1982, and U.S. application Ser. No. 548,850, filed Nov. 4, 1983), filed in the name of Sandoz AG discloses heterocyclic analogs of mevalono lactone and derivatives thereof having the structure

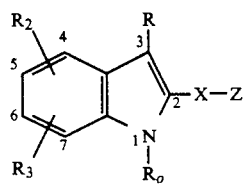

wherein one of R and $R_o$ is

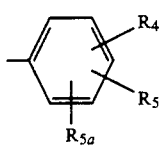

and the other is primary or secondary $C_{1-6}$ alkyl, $C_{3-6}$ cycloalkyl or phenyl-$(CH_2)_m-$, wherein $R_4$ is hydrogen, $C_{1-4}$ alkyl, $C_{1-4}$ alkoxy, (except t-butoxy), trifluoromethyl, fluoro, chloro, phenoxy or benzyloxy, $R_5$ is hydrogen, $C_{1-3}$ alkyl, $C_{1-3}$ alkoxy, trifluoromethyl, fluoro, chloro, phenoxy or benzyloxy, $R_{5a}$ is hydrogen, $C_{1-2}$ alkyl, $C_{1-2}$ alkoxy, fluoro or chloro, and m is 1, 2 or 3, with the provisos that both $R_5$ and $R_{5a}$ must be hydrogen when $R_4$ is hydrogen, $R_{5a}$ must be hydrogen when $R_5$ is hydrogen, not more than one of $R_4$ and $R_5$ is trifluoromethyl, not more than one of $R_4$ and $R_5$ is phenoxy and not more than one of $R_4$ and $R_5$ is benzyloxy, $R_2$ is hydrogen, $C_{1-4}$ alkyl, $C_{3-6}$ cycloalkyl, $C_{1-4}$ alkoxy (except t-butoxy), trifluoromethyl, fluoro, chloro, phenoxy or benzyloxy, $R_3$ is hydrogen, $C_{1-3}$ alkyl, $C_{1-3}$ alkoxy, trifluoromethyl, fluoro, chloro, phenoxy or benzyloxy, with the provisos that $R_3$ must be hydrogen when $R_2$ is hydrogen, not more than one of $R_2$ and $R_3$ is trifluoromethyl, not more than one of $R_2$ and $R_3$ is phenoxy, and not more than one of $R_2$ and $R_3$ is benzyloxy.

X is $-(CH_2)_n-$ or $-CH=CH-$ (n=0, 1, 2 or 3),

Z is

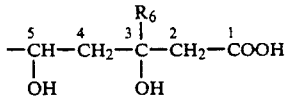

wherein $R_6$ is hydrogen or $C_{1-3}$ alkyl in free acid form or in the form of a physiologically-hydrolysable and -acceptable ester of a δ lactone thereof or in salt form.

GB 2162-179-A discloses naphthyl analogues of mevalolactone useful as cholesterol biosynthesis inhibitors having the structure

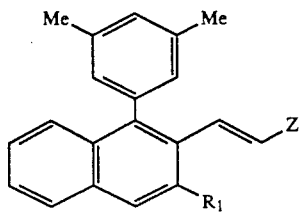

wherein
$R_1 = 1-3C$ alkyl;
Z is a gp. of formula $Z_1$ or $Z_2$:

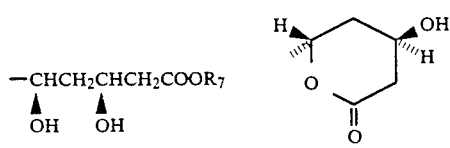

(Z$_1$)      (Z$_2$)

$R_7$=H, a hydrolysable ester gp. or a cation.

European Patent No. 164-698-A discloses preparation of lactones useful as anti-hypercholesterolemic agents by treating an amide with an organic sulphonyl halide $R^5SO_2X$, then removing the protecting group Pr.

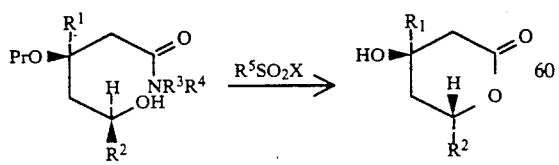

wherein
X=halo;
Pr=a carbinol-protecting group;
$R^1$=H or $CH_3$;

$R^3$, $R^4$=H, 1-3C alkyl or phenyl-(1-3C alkyl), the phenyl being optionally substituted by 1-3C alkyl, 1-3C alkoxy or halo;

$R^2$=a group of formula (A) or (B):

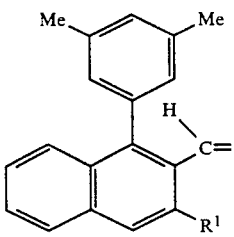

$Q = R^6—\underset{CH_3}{\overset{|}{C}}—$    or    $R^6—\overset{|}{\underset{|}{CH}};$ $R^6$=H or OH;
R=H or $CH_3$;
a, b, c and d=optional double bonds;
$R^7$=phenyl or benzyloxy, the ring in each case being optionally substituted by 1-3C alkyl or halo;
$R^8$, $R^9$=1-3C alkyl or halo;
$R^5$=1-3C alkyl, phenyl or mono- or di-(1-3C alkyl)-phenyl.

Anderson, Paul Leroy, Ger. Offen. De 3,525,256 discloses naphthyl analogs of mevalonolactones of the structure

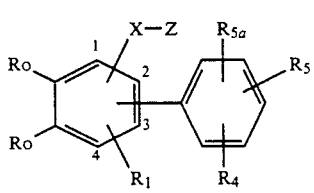

I          Q          Q' wherein $R^1$ is alkyl, Z=Q, $Q^1$; $R^7$=H, or a hydrolyzable ester group useful as inhibitors of cholesterol biosynthesis and in treatment of atherosclerosis.

WO 8402-903 (based on U.S. application Ser. No. 460,600, filed Jan. 24, 1983) filed in the name of Sandoz AG discloses mevalono-lactone analogues useful as hypolipoproteinaemic agents having the structure wherein the two groups Ro together form a radical of formula

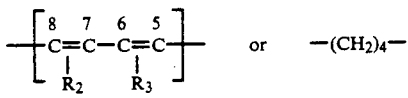 or —(CH$_2$)$_4$— wherein

R$_2$ is hydrogen, C$_{1-4}$ alkyl, C$_{1-4}$ alkoxy, (except t-butoxy), trifluoromethyl, fluoro, chloro, phenoxy or benzyloxy, R$_3$ is hydrogen, C$_{1-3}$ alkyl, C$_{1-3}$ alkoxy, trifluoromethyl, fluoro, chloro, phenoxy or benzyloxy, with the provisos that not more than one of R$_2$ and R$_3$ is trifluoromethyl, not more than one of R$_2$ and R$_3$ is phenoxy, and not more than one of R$_2$ and R$_3$ is benzyloxy, R$_1$ is hydrogen, C$_{1-6}$ alkyl, fluoro, chloro or benzyloxy, R$_4$ is hydrogen, C$_{1-4}$ alkyl, C$_{1-4}$ alkoxy, (except t-butoxy), trifluoromethyl, fluoro, chloro, phenoxy or benzyloxy, R$_5$ is hydrogen, C$_{1-3}$ alkyl, C$_{1-3}$ alkoxy, trifluoromethyl, fluoro, chloro, phenoxy or benzyloxy, R$_{5a}$ is hydrogen, C$_{1-2}$ alkyl, C$_{1-2}$ alkoxy, fluoro or chloro, and with the provisos that not more than one of R$_4$ and R$_5$ is trifluoromethyl, not more than one of R$_4$ and R$_5$ is phenoxy and not more than one of R$_4$ and R$_5$ is benzyloxy, X is —(CH$_2$)$_n$—,

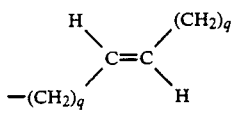

wherein n is 0, 1, 2 or 3 and both q's are 0 or one is 0 and the other is 1,

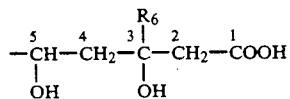                                            II wherein R$_6$ is hydrogen or C$_{1-3}$ alkyl, with the general proviso that —X—Z and the R$_4$ bearing phenyl group are ortho to each other; in free acid form or in the form of a physiologically-hydrolysable and acceptable ester or a δ lactone thereof or in salt form.

U.S. Pat. No. 4,613,610 to Wareing (assigned to Sandoz) discloses a series of 7-pyrazolo-3,5-dihydrohept-6-enoic acid HMG-CoA reductase inhibitors of the structure

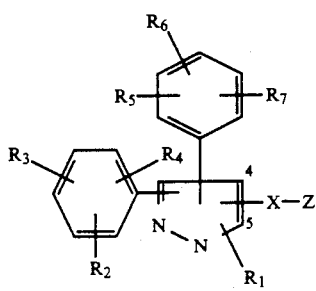

wherein

R$_1$ is C$_{1-6}$alkyl not containing an asymmetric carbon atom, each of R$_2$ and R$_5$ is independently hydrogen, C$_{1-3}$alkyl, n-butyl, i-butyl, t-butyl, C$_{1-3}$alkoxy, n-butoxy, i-butoxy, trifluoromethyl, fluoro, chloro, phenyl, phenoxy or benzyloxy, each of R$_3$ and R$_6$ is independently hydrogen, C$_{1-3}$alkyl, C$_{1-3}$alkoxy, trifluoromethyl, fluoro, chloro, phenoxy or benzyloxy, each of R$_4$ and R$_7$ is independently hydrogen, C$_{1-2}$alkyl, C$_{1-2}$alkoxy, fluoro or chloro, with the provisos that not more than one of R$_2$ and R$_3$ is trifluoromethyl, not more than one of R$_2$ and R$_3$ is phenoxy, not more than one of R$_2$ and R$_3$ is benzyloxy, not more than one of R$_5$ and R$_6$ is trifluoromethyl, not more than one of R$_5$ and R$_6$ is phenoxy, and not more than one of R$_5$ and R$_6$ is benzyloxy, X is —(CH$_2$)$_m$—, —CH=CH—, —CH=CH—CH$_2$— or —CH$_2$—CH=CH—, wherein m is 0, 1, 2 or 3, and Z is

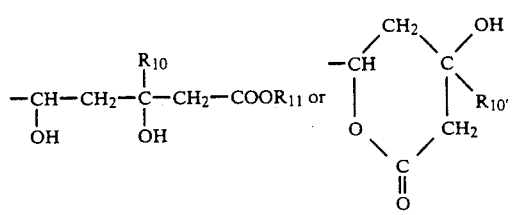

wherein

R$_{10}$ is hydrogen or C$_{1-3}$alkyl, and R$_{11}$ is hydrogen, R$_{12}$ or M, wherein R$_{12}$ is a physiologically acceptable and hydrolyzable ester group, and M is a cation, with the provisos that (i) the —X—Z group is in the 4- or 5-position of the pyrazole ring, and (ii) the R$_1$ group and the —X—Z group are ortho to each other.

WO 8607-054A (Sandoz-Erfindungen) discloses imidazole analogues of mevalonolactone, useful for treating hyperlipoproteinaemia and atherosclerosis, which have the formula

                                            (I)

R$_1$=alkyl, cycloalkyl, adamantyl-1 or R$_4$, R$_5$, R$_6$-substituted phenyl (gp. A);

R$_2$=alkyl, cycloalkyl, adamantyl-1 or R$_7$, R$_8$, R$_9$-substituted phenyl (gp. B);

R$_3$=H, alkyl, cycloalkyl, adamantyl-1, styryl or R$_{10}$, R$_{11}$, R$_{12}$-substituted phenyl (gp, C);

X=—(CH$_2$)$_m$—, —CH=CH—, —CH=CH—CH$_2$— or —CH$_2$—CH=CH—;

m=0–3;

Z=—CH(OH)—CH$_2$—C(R$_{13}$)(OH)—CH$_2$—COOR$_{14}$ (gp. a), —Q—CH$_2$—C(R$_{13}$)(OH)—CH$_2$—COOR$_{14}$ (gp. c) or a gp. of formula (b):

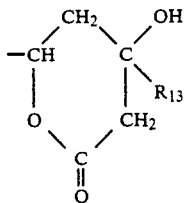

Q=CO or —C(OR$_{15}$)$_2$—;
R$_{15}$=primary or sec. alkyl; each R$_{15}$ being the same; or R$_{15}$+R$_{15}$=(CH$_2$)$_2$ or (CH$_2$)$_3$;
R$_{13}$=H or 1-3C alkyl;
R$_{14}$=H, R$_{16}$ or M;
R$_{16}$=ester gp.;
M=cation;
provided that Z may be gp. (c) only when X is CH=CH or CH$_2$—CH=CH and/or when R$_{13}$=1-3C alkyl;
R$_4$, R$_7$ and R$_{10}$=1-3C alkyl, n-, i- or t-butyl, 1-3C alkoxy, n- or i-butoxy, CF$_3$, F, Cl, Br, phenyl, phenoxy or benzyloxy;
R$_5$, R$_8$ and R$_{11}$=H, 1-3C alkyl, 1-3C alkoxy, CF$_3$, F, Cl, Br, COOR$_{17}$, N(R$_{19}$)$_2$, phenoxy or benzyloxy;
R$_{17}$=H, R$_{18}$ or M;
R$_{18}$=1-3C alkyl, n, i- or t-butyl or benzyl;
R$_{19}$=alkyl;
R$_6$, R$_9$ and R$_{12}$=H, 1-2C alkyl, 1-2C alkoxy, F or Cl;
provided that (1) not more than one substituent of each of gps. A, B and C is CF$_3$, not more than one substituent of each of gps. A, B and C is phenoxy, and not more than one substituent of each of gps, A, B and C is benzyloxy;

(2) when Z is gp. (c; Q=C(OR$_{15}$)$_2$), the compound is in free base form and either (i) R$_{14}$ is R$_{16}$ and each R$_{17}$ is independently R$_{18}$ or (ii) R$_{14}$ is M and each R$_{17}$ is independently R$_{18}$ or M; and (3) when R$_{14}$ and/or at least one R$_{17}$ is M, the compound is in free base form.

Unless otherwise stated, all "alkyl" gps. are 1-6C and do not contain an asymmetric C; and "cycloalkyl" has 3-7C.

WO 8603-488-A (Sandoz AG) discloses indene analogues of mevalolactone, useful as hypolipoproteinaemia and anti-atherosclerotic agents, in free acid form or in the form of an ester or delta-lactone or in salt form which have the formula

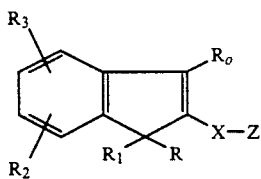
(I)

R=H or primary or secondary 1-6C alkyl;
R$_1$=primary or secondary 1-6C alkyl;
or R+R$_1$=(CH$_2$)$_m$ or (Z)—CH$_2$—CH=CH—CH$_2$;
m=2-6;
R$_o$=1-6C alkyl, 3-7C cycloalkyl or R$_4$, R$_5$, R$_6$-substituted phenyl;
R$_2$, R$_4$=H, 1-4C alkyl, 1-4C alkoxy (except t-butoxy), CF$_3$, F, Cl, phenoxy or benzyloxy;
R$_3$ and R$_5$=H, 1-3C alkyl, 1-3C alkoxy, CF$_3$, F, Cl, phenoxy or benzyloxy;
R$_6$=H, 1-2C alkyl, 1-2C alkoxy, F or Cl;
provided that there may only be one each of CF$_3$, phenoxy or benzyloxy on each of the phenyl and indene rings;
X=(CH$_2$)$_n$ or —(CH$_2$)$_q$—CH=CH(CH$_2$)$_q$—;
n=1-3;
both q's=0, or one is 0 and the other is 1;
Z=—Q—CH$_2$—C(R$_{10}$)(OH)—CH$_2$COOH, in free acid form or in the form of an ester or delta-lactone or salt;
Q=CO, —C(OR$_7$)$_2$— or CHOH;
R'$_{7s}$=the same primary or secondary 1-6C alkyl, or together are (CH$_2$)$_2$ or (CH$_2$)$_3$;
R$_{10}$=H or 1-3C alkyl;
provided that Q may be other than CHOH only when X is CH=CH or CH$_2$—CH=CH and/or R$_{10}$ is 1-3C alkyl.

U.S. Pat. No. 4,647,576 to Hoefle et al (Warner Lambert) discloses new C- and N-substituted pyrrole(s), useful as hypolipidaemic and hypocholesterolaemic agents, which have the formula

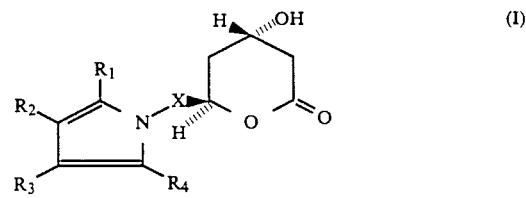
(I)

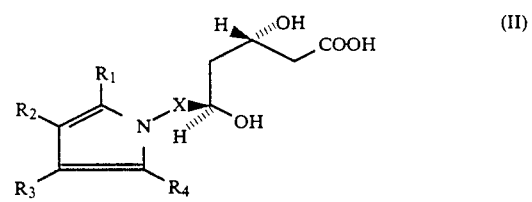
(II)

X=—CH$_2$—, —CH$_2$CH$_2$— or —CH(CH$_3$)CH$_2$—;
R$_1$=1- or 2-naphthyl; cyclohexyl; norbornenyl; phenyl optionally substituted by F, Cl, OH, CF$_3$, 1-4C alkyl, 1-4C alkoxy or 2-8C alkanoyloxy; 2-, 3- or 4-pyridinyl or their N-oxides; or

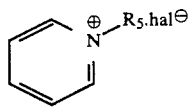

R$_5$=1-4C alkyl;
hal=chloride, bromide or iodide;
R$_2$ and R$_3$=H, Cl, Br, CN, CF$_3$, phenyl, 1-4C alkyl, 2-8C carboalkoxy, —CH$_2$OR$_6$ or —CH$_2$OCONHR$_7$;
R$_6$=H or 1-6C alkanoyl;
R$_7$=alkyl or phenyl optionally substituted by Cl, Br or 1-4C alkyl;
or R$_2$ and R$_3$ together=—(CH$_2$)$_n$—, —CH$_2$OCH$_2$—, —CON(R$_8$)CO— or —CON(R$_9$)N(R$_{10}$)CO—;
n=3 or 4;
R$_8$=H, 1-6C alkyl, phenyl or benzyl;
R$_9$ and R$_{10}$=H, 1-4C alkyl or benzyl;
R$_4$=1-4C alkyl, cyclopropyl, cyclobutyl or CF$_3$.

European patent application 0 221 025 A1 (Sandoz AG) discloses heterocyclic analogs of mevalonolactone and derivatives thereof having the formula

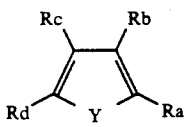

wherein

Ra is a group —X—Z, Rb is $R_2$, Rc is $R_3$, Rd is $R_4$ and Y is a group

or

Ra is $R_1$, Rb is a group —X—Z, Rc is $R_2$, Rd is $R_3$ and Y is O, S or a group

$R_1$, $R_2$, $R_3$ and $R_4$ independently are $C_{1-4}$ alkyl not containing an asymmetric carbon atom, $C_{3-7}$cycloalkyl or a ring

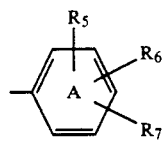

or in the case of $R_3$ and $R_4$ additionally hydrogen or for $R_3$ when Y is O or S

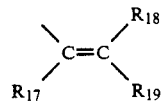

whereby $R_{17}$ is hydrogen or $C_{1-3}$alkyl and $R_{18}$ and $R_{19}$ are independently hydrogen, $C_{1-3}$alkyl or phenyl; each $R_5$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, bromo, phenyl, phenoxy or benzyloxy; each $R_6$ is independently hydrogen, $C_{1-3}$alkyl, $C_{1-3}$alkoxy, trifluoromethyl, fluoro, chloro, bromo, phenoxy or benzyloxy and each $R_7$ is independently hydrogen, $C_{1-2}$alkyl, $C_{1-2}$alkoxy, fluoro or chloro with the proviso that there may only be one each of trifluoromethyl, phenoxy or benzyloxy in each ring A present. X is $(CH_2)_m$ or $(CH_2)_qCH=CH(CH_2)_q$, m is 0, 1, 2 or 3 and both q's are 0 or one is 0 and the other is 1.

Z is

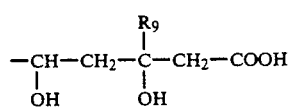

wherein $R_9$ is hydrogen or $C_{1-3}$alkyl, in free acid form or in the form of an ester of β-lactone thereof or in salt form as appropriate which compounds are indicated for use as hypolipoproteinemic and anti-antherosclerotic agents.

Tetrahedron Letters, 29, 929, 1988, discloses the synthetic of a 3-hydroxy-3-methylglutaryl coenzyme A reductase inhibitor of the structure

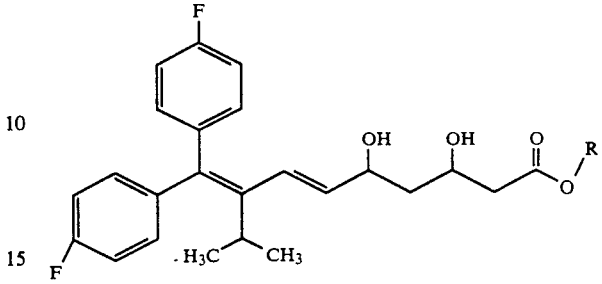

where R is Na or $C_2H_5$.

European patent application 127,848-A (Merck & Co., Inc.) discloses derivatives of 3-hydroxy-5-thia-ω-aryl-alkanoic acids having the structural formula:

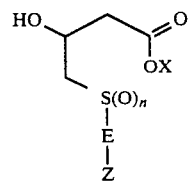

wherein

Z is:

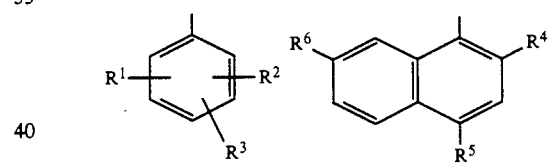

n is 0, 1 or 2;

E is —$CH_2$—, —$CH_2$—$CH_2$—, —$CH_2$—$CH_2$—$CH_2$—, —CH=CH—$CH_2$—; or —$CH_2$—CH=CH—;

$R_1$, $R_2$ and $R_3$ are, e.g., hydrogen, chloro, bromo, fluoro, $C_1$-alkyl, phenyl, substituted phenyl or $OR_7$ in which $R_7$ is, e.g., hydrogen, $C_{2-8}$alkanoyl, benzoyl, phenyl, substituted phenyl, $C_{1-9}$alkyl, cinnamyl, $C_{1-4}$haloalkyl, allyl, cycloalkyl-$C_{1-3}$alkyl, adamantyl-$C_{1-3}$-alkyl, or phenyl $C_{1-3}$ alkyl;

$R^4$, $R^5$ and $R^6$ are hydrogen, chloro, bromo, fluoro or $C_{1-3}$ alkyl; and X is, e.g., hydrogen, $C_{1-3}$ alkyl, a cation derived from an alkali metal or is ammonium.

Those compounds have antihypercholesterolemic activity by virtue of their ability to inhibit 3-hydroxy-3-methylglutaryl-coenzyme A (HMG-CoA) reductase and antifungal activity.

French patent application 2,596,393 A filed on Apr. 1, 1986 (Sanofi SA) discloses 3-carboxy-2-hydroxy-propane-phosphonic acid derivatives including salts thereof which are useful as hypolipaemic agents and have the formula:

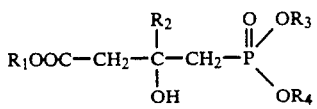

wherein $R_1$ and $R_2$=H, lower alkyl or optionally substituted aralkyl;

$R_3$ and $R_4$=H, lower alkyl or optionally substituted aryl or aralkyl.

These compounds are disclosed as giving greater reductions in cholesterol, triglyceride and phospholipid levels than meglutol.

European patent application 142,146-A (Merck & CO., Inc) discloses mevinolin-like compounds of the structural formula:

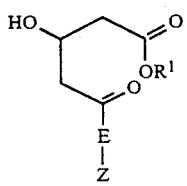

wherein:

$R^1$ is e.g., hydrogen or $C_{1-4}$alkyl;

E is —$CH_2CH_2$, —CH=CH—, or —$(CH_2)_r$—; and

Z is

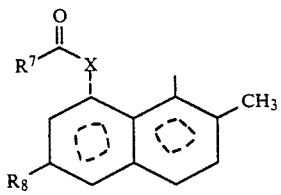

(1)

wherein

X is —O— or —$NR^9$ wherein $R^9$ is hydrogen or $C_{1-3}$alkyl;

$R^7$ is $C_{2-8}$alkyl; and $R^8$ is hydrogen or $CH_3$;

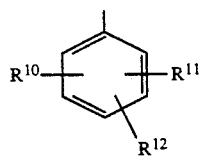

(2)

wherein $R^{10}$, $R^{11}$ and $R^{12}$ are independently, e.g., hydrogen, halogen or $C_{1-4}$alkyl;

3)

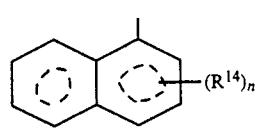

wherein n is 0–2 and $R^{14}$ is halo or $C_{1-4}$alkyl; or

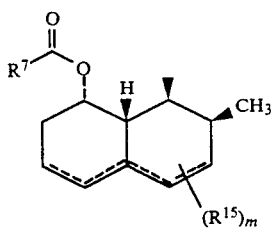

(4)

These compounds are HMG-CoA reductase inhibitors.

British Patent 2205838 discloses HMG CoA reductase inhibitors which have the formula

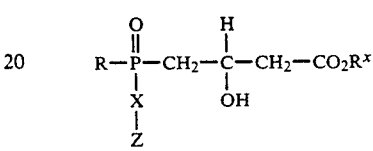

wherein

R is OH or lower alkoxy;

$R^x$ is H or lower alkyl;

X is $CH_2$, —$CH_2CH_2$—, —$CH_2CH_2CH_2$—, —CH=CH—, —C≡C— or —$CH_2O$— (where O is linked to Z);

Z is a hydrophobic anchor;

and including pharmaceutically acceptable salts thereof.

Examples of hydrophobic anchors which are included in this copending application include

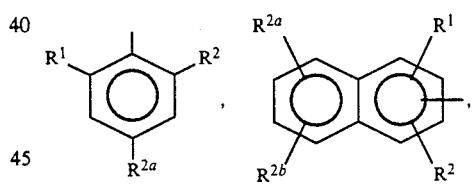

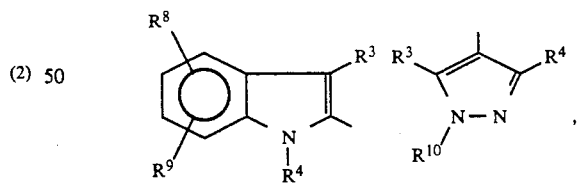

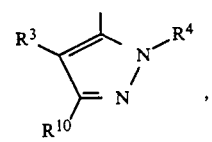

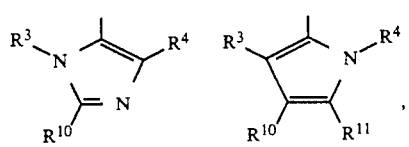

-continued

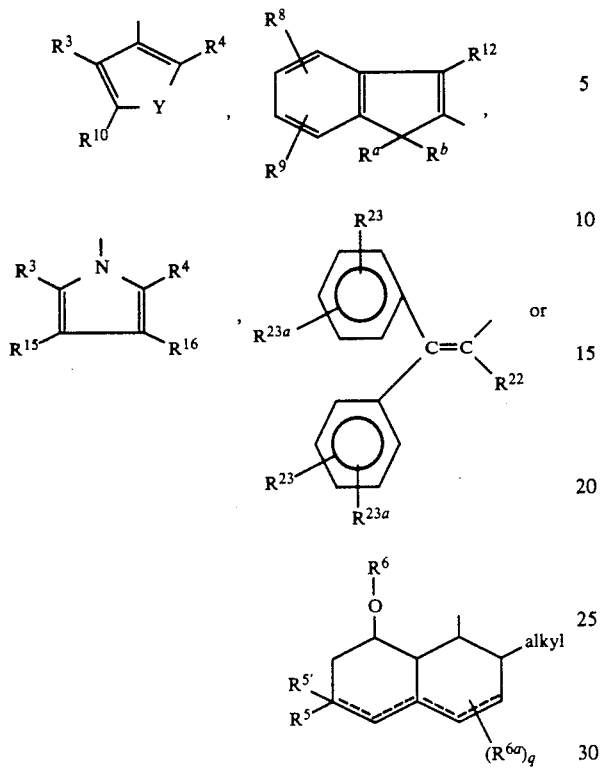

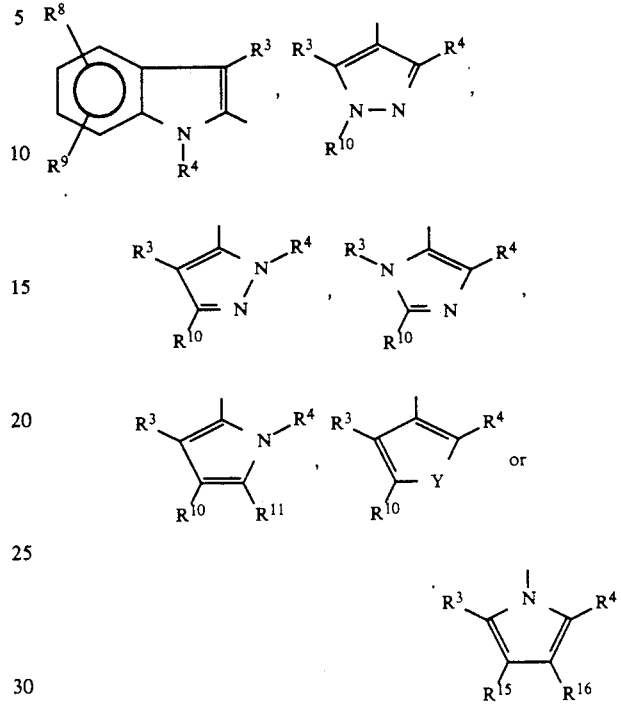

wherein the dotted lines represent optional double bonds, wherein $R^1$, $R^2$, $R^{2a}$ and $R^{2b}$ may be the same or different and are each independently selected from H, halogen, lower alkyl, haloalkyl, phenyl, substituted phenyl or $OR^v$ wherein $R^v$ 1 is H, alkanoyl, benzoyl, phenyl, halophenyl, phenyl-lower alkyl, lower alkyl, cinamyl, haloalkyl, allyl, cycloalkyl-lower alkyl, adamantyl-lower alkyl or substituted phenyl-lower alkyl. Where Z is

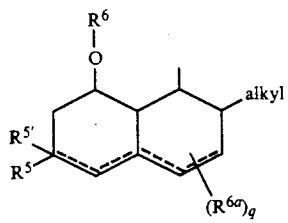

$R^5$ and $R^{5'}$ are the same or different and are H, lower alkyl or OH;
$R^6$ is lower

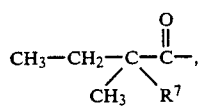

such as

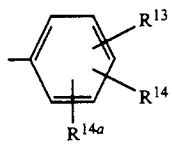

or aryl$CH_2$—;

$R^{6a}$ is lower alkyl, hydroxy, oxo or halogen; q is 0, 1, 2 or 3, and $R^7$ is H or lower alkyl.
Where Z is one of $R^3$ and $R^4$ is and the other is lower alkyl, cycloalkyl or phenyl-$(CH_2)_p$—, p is 0, 1, 2, 3 or 4;
wherein $R^{13}$ is hydrogen, lower alkyl, lower alkoxy, (except t-butoxy), halogen, phenoxy or benzyloxy;
$R^{14}$ is hydrogen, lower alkyl, lower alkoxy, halogen, phenoxy or benzyloxy;
$R^{14a}$ is hydrogen, lower alkyl, lower alkoxy, or halogen; and
with the provisos that both $R^{14}$ and $R^{14a}$ must be hydrogen when $R^{13}$ is hydrogen, $R^{14a}$ must be hydrogen when $R^{14}$ is hydrogen, not more than one of $R^{13}$ and $R^{14}$ is trifluoromethyl, not more than one of $R^{13}$ and $R^{14}$ is phenoxy and not more than one of $R^{13}$ and $R^{14}$ is benzyloxy;
$R^8$ is hydrogen, $C_{1-4}$ alkyl, $C_{3-6}$ cycloalkyl, $C_{1-4}$ alkoxy (except t-butoxy), trifluoromethyl, fluoro, chloro, phenoxy or benzyloxy;
$R^9$ is hydrogen, $C_{1-3}$ alkyl, $C_{1-3}$ alkoxy, trifluoromethyl, fluoro, chloro, phenoxy or benzyloxy, with the provisos that $R^9$ must be hydrogen when $R^8$ is hydrogen, not more than one of $R^8$ and $R^9$ is trifluoromethyl, not more than one of $R^8$ and $R^9$ is phenoxy, and not more than one of $R^8$ and $R^9$ is benzyloxy.

$R^{10}$ and $R^{11}$ are independently selected from hydrogen, alkyl, cycloalkyl, adamantyl-1 or

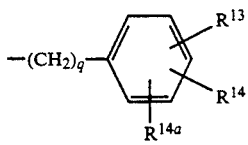

where $R^{13}$, $R^{14}$ and $R^{14a}$ are as defined above and q=0, 1, 2, 3 or 4.

Y is O, S or N-$R^{10}$.

Where Z is

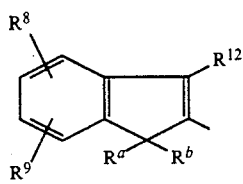

$R^a$ is H or primary or secondary 1-6C alkyl;
$R^b$ is primary or secondary 1-6C alkyl;
or $R^a + R^b$ is $(CH_2)_r$ or (cis)—$CH_2$—CH=CH—$CH_2$;
r=2, 3, 4, 5 or 6;
$R^{12}$ is lower alkyl, cycloalkyl or

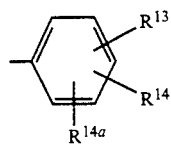

wherein $R^8$, $R^9$, $R^{13}$, $R^{14}$ and $R^{14a}$ are as defined above.

When Z is

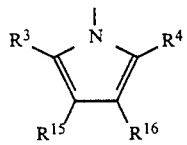

$R^{15}$ and $R^{16}$ are both H, Cl, Br, CN, $CF_3$, phenyl, 1-4C alkyl, 2-8C alkoxycarbonyl, —$CH_2OR^{17}$ or —$CH_2OCONHR^{18}$;

$R^{17}$ is H or 1-6C alkanoyl;

$R^{18}$ is alkyl or phenyl optionally substituted by F, Cl, Br or 1-4C alkyl;

or $R^{15}$ and $R^{16}$ taken together are —$(CH_2)_s$—, —$CH_2OCH_2$—, —$CON(R^{19})CO$—, or —$CON(R^{20})N(R^{21})CO$—;

s=3 or 4;

$R^{19}$=H, 1-6C alkyl, phenyl or benzyl;

$R^{20}$ and $R^{21}$ are H, 1-4C alkyl or benzyl; with the added proviso that when Z is

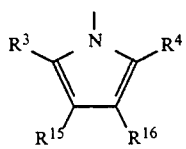

X can only be —$CH_2$—, —$CH_2CH_2$— or —$CH_2CH_2CH_2$.

Where Z is

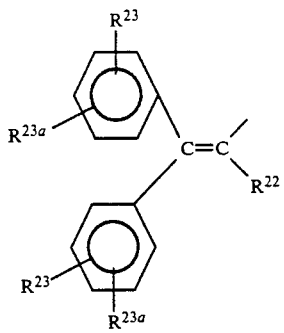

$R^{22}$ is lower alkyl, cycloalkyl, adamantyl-1

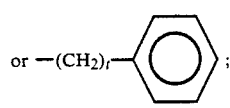

t=1, 2, 3 or 4;

$R^{23}$ and $R^{23a}$ are the same or different and are each independently selected from hydrogen, lower alkyl, lower alkoxyl (except t-butoxy), halogen, phenoxy or benzyloxy; and with the provisos that $R^{23a}$ must be hydrogen when $R^{23}$ is hydrogen, not more than one of $R^{23}$ and $R^{23a}$ is trifluoromethyl, not more than one of $R^{23}$ and $R^{23a}$ is phenoxy, and not more than one of $R^{23}$ and $R^{23a}$ is benzyloxy.

Where X is —$CH_2O$— (carbon attached to P and O attached to Z), the hydrophobic anchor Z will be a phenyl or naphthalene type anchor such as

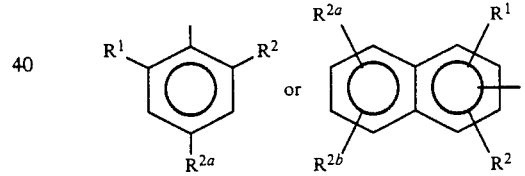

International Publication No. WO 88/01997 (PCT/EP87/00511) published March 24, 1988, filed by Sandoz on behalf of Anderson et al discloses aza-indole and indolizine derivatives which are useful as hypolipoproteinaemic and antiatherosclerotic agents and have the formula

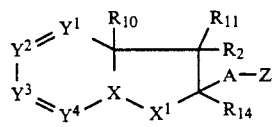

I wherein
either one of $Y^1$-$Y^4$ is —N—, and the others are —CH—

X is

$X^1$ is

and $R_{10}$ and $R_{15}$, and $R_{11}$ and $R_{14}$ form bonds $R_1$ is a primary or secondary $C_{1-6}$alkyl, not containing an asymmetric carbon atom;

$R_2$ is a)

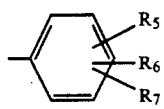

b) a primary or secondary $C_{1-6}$alkyl, not containing an asymmetric carbon atom c) $C_{3-6}$ cycloalkyl or d) phenyl-$(CH_2)_m$— wherein $R_5$ is hydrogen, $C_{1-3}$alkyl, n-butyl, i-butyl t-butyl, $C_{1-3}$alkoxy, n-butoxy, i-butoxy, trifluoromethyl fluoro, chloro, phenoxy or benzyloxy;

$R_6$ is hydrogen, $C_{1-3}$alkyl, $C_{1-3}$alkoxy, fluoro, chloro, trifluoromethyl, phenoxy or benzyloxy;

$R_7$ is hydrogen, $C_{1-2}$alkyl, $C_{1-2}$alkoxy, fluoro or chloro;

m is 1, 2 or 3;

with the proviso that not more than one of $R_5$ and $R_6$ is trifluoromethyl, not more than one of $R_5$ and $R_6$ is phenoxy, and not more than one of $R_5$ and $R_6$ is benzyloxy; or $Y^1-Y^4$ are —CH—

X is —N—

$X^1$ is

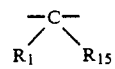

and $R_{14}$ and $R_{15}$, and $R_{10}$ and $R_{11}$ form bonds; each of $R_1$ and $R_2$ is, independently, as defined under $R_2$ above, and $R_2$ may additionally be hydrogen:

A is a)

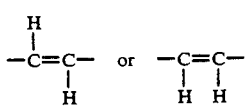

b) —$(CH_2)_n$— wherein n is 1, 2 or 3

Z is

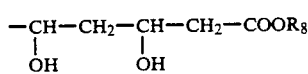    (a)

or

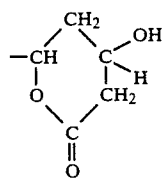    (b)

and in which $R_8$ is hydrogen, $R_9$ or M, wherein $R_9$ is a physiologically acceptable and hydrolysable ester group, and M is a pharmaceutically acceptable cation.

DESCRIPTION OF THE INVENTION

In accordance with the present invention, there is provided phosphorus-containing compounds which inhibit the enzyme 3-hydroxy-3-methylglutaryl-coenzyme A reduction (HMG-CoA REductase) and thus are useful as hypocholesterolemic agents and include the following moiety $$-\underset{\underset{Z}{\overset{\overset{O}{\|}}{\underset{X}{P}}}}{-}CH_2-\underset{\underset{OH}{|}}{CH}-CH_2-CO-$$

wherein X is —$(CH_2)_a$—, —CH=CH—, or —C≡C—, "a" is 1 2 or 3, and Z is

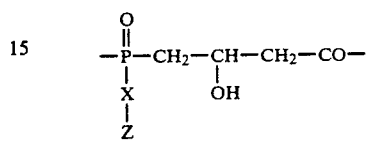

wherein one of $R^1$ and $R^2$ is substituted phenyl (including a halo or lower alkyl substituent) and the other of $R^1$ and $R^2$ is lower alkyl; and $R^3$ and $R^4$ together are –(CH=CH–)$_2$ or –(CH$_2$–)$_4$ are and joined to complete a six-membered carbocyclic ring, namely

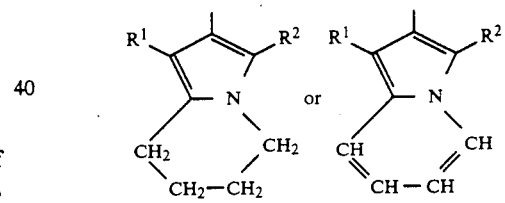

In preferred embodiments, the compounds of the invention have the formula I

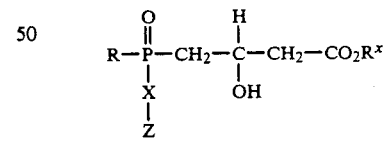    I wherein

R is OH or lower alkoxy;

$R^x$ is H or lower alkyl;

X is $CH_2$, —$CH_2CH_2$—, —$CH_2CH_2CH_2$—, —CH=CH—, or —C≡C—; Z is

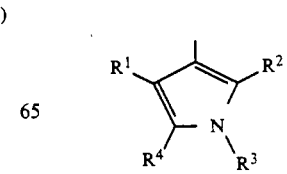

and including pharmaceutically acceptable salts thereof.

The terms "salt" and "salts" refer to basic salts formed with inorganic and organic bases. Such salts include ammonium salts, alkali metal salts like, lithium, sodium and potassium salts (which are preferred), alkaline earth metal salts like the calcium and magnesium salts, salts with organic bases, such as amine like salts, e.g., dicyclohexylamine salt, benzathine, N-methyl-D-glucamine, hydrabamine salts, salts with amino acids like arginine, lysine and the like. The nontoxic, pharmaceutically acceptable salts are preferred, although other salts are also useful, e.g., in isolating or purifying the product.

Thus, the compounds of formula I encompass

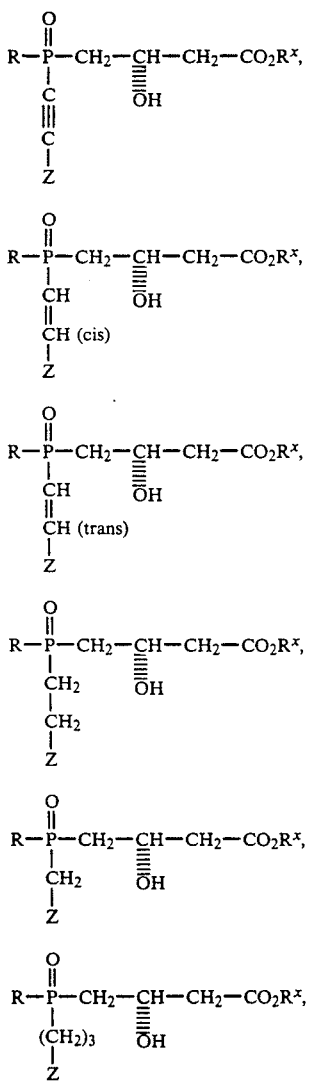

The term "lower alkyl" or "alkyl" as employed herein alone or as part of another group includes both straight and branched chain hydrocarbons, containing 1 to 12 carbons in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkylaryl substituent, a haloaryl substituent, a cycloalkyl substituent, an alkylcycloalkyl substituent, hydroxy, and alkylamino substituent, an alkanoylamino substituent, an arylcarbonylamino substituent, a nitro substituent, a cyano substituent, a thiol substituent or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1, 2 or 3 lower alkyl groups, halogens (Cl, Br or F), 1, 2 or 3 lower alkoxy groups, 1, 2 or 3 hydroxy groups, 1, 2 or 3 phenyl groups, 1, 2 or 3 alkanoyloxy group, 1, 2 or 3 benzoyloxy groups, 1, 2 or 3 haloalkyl groups, , 2 or 3 halophenyl groups, 1, 2 or 3 allyl groups, 1, 2 or 3 cycloalkylalkyl groups, 1, 2 or 3 adamantylalkyl groups, 1, 2 or 3 alkylamino groups, 1, 2 or 3 alkanoylamino groups, 1, 2 or 3 arylcarbonylamino groups, 1, 2 or 3 amino groups, 1, 2 or 3 nitro groups, 1, 2 or 3 cyano groups, 1, 2 or 3 thiol groups, and/or 1, 2 or 3 alkylthio groups with the aryl group preferably containing 3 substituents.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy", or "aryloxy" or "aralkoxy" as employed herein alone or as part of another group includes any of the above lower alkyl, alkyl, aralkyl or aryl groups linked to an oxygen atom.

The term "lower alkylthio", "alkylthio", "arylthio" or "aralkylthio" as employed herein alone or as part of another group includes any of the above lower alkyl, alkyl, aralkyl or aryl groups linked to a sulfur atom.

The term "lower alkylamino", "alkylamino", "arylamino", "arylalkylamino" as employed herein alone or as part of another group includes any of the above lower alkyl, alkyl, aryl or arylalkyl groups linked to a nitrogen atom.

The term "alkanoyl" as used herein as part of another group refers to lower alkyl linked to a carbonyl group.

The term "halogen" or "halo" as used herein refers to chlorine, bromine, fluorine, iodine and $CF_3$, with chlorine or fluorine being preferred.

Preferred are those compounds of formula I which have the following structure

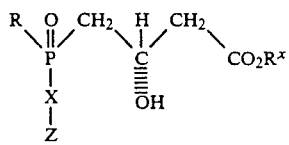

wherein
R is OH, OLi or CH₃O; R^x is Li or H;
X is —CH₂CH₂—, —CH=CH—, or —C≡C— and
Z is
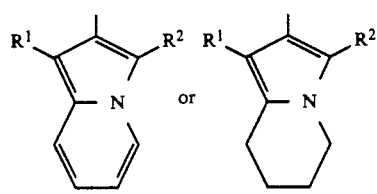
wherein one of $R^1$ and $R^2$ is phenyl or phenyl which includes an alkyl and/or halo substituent, and the other of $R^1$ and $R^2$ is lower alkyl such as isopropyl.
The compounds of formula I of the invention may be prepared according to the following reaction sequence and description thereof.
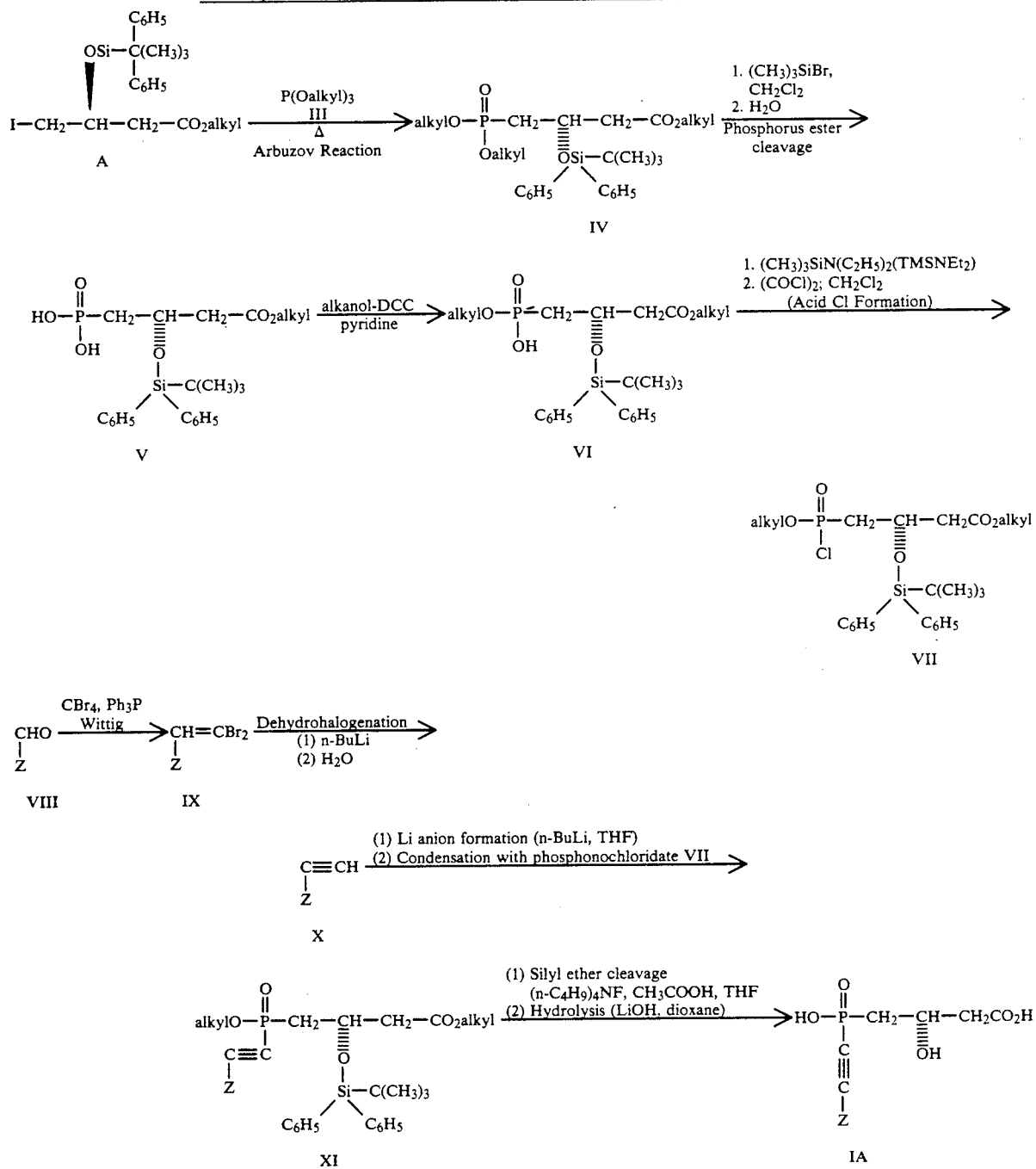

-continued
Reaction Sequence A.
Preparation of Compounds of Formula I where X is —CH=CH— or C≡C—
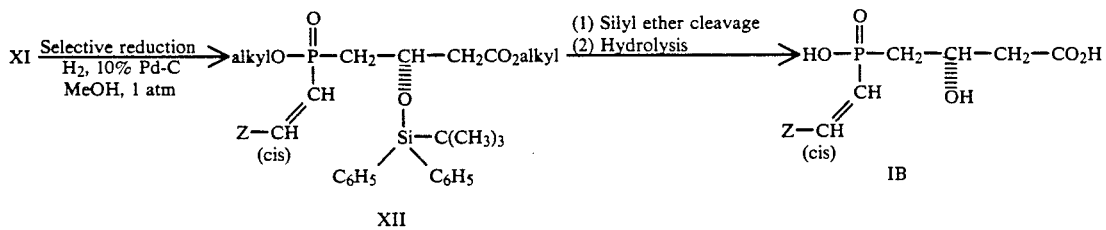
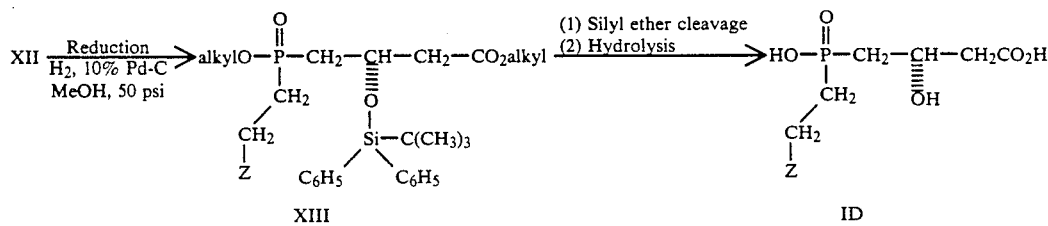
A[1]. Preparation of acetylene starting material X where $R^3$ and $R^4$ together are $-(CH_2)_n-$
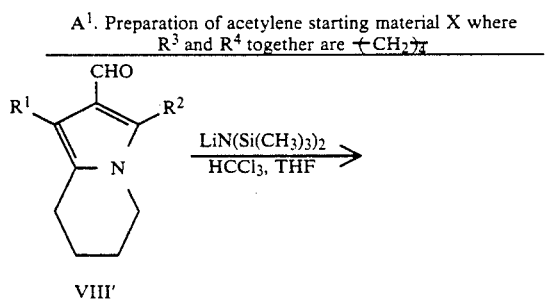
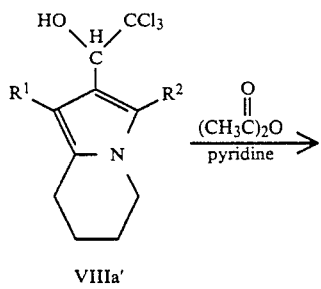
-continued
A[1]. Preparation of acetylene starting material X where $R^3$ and $R^4$ together are $-(CH_2)_n-$
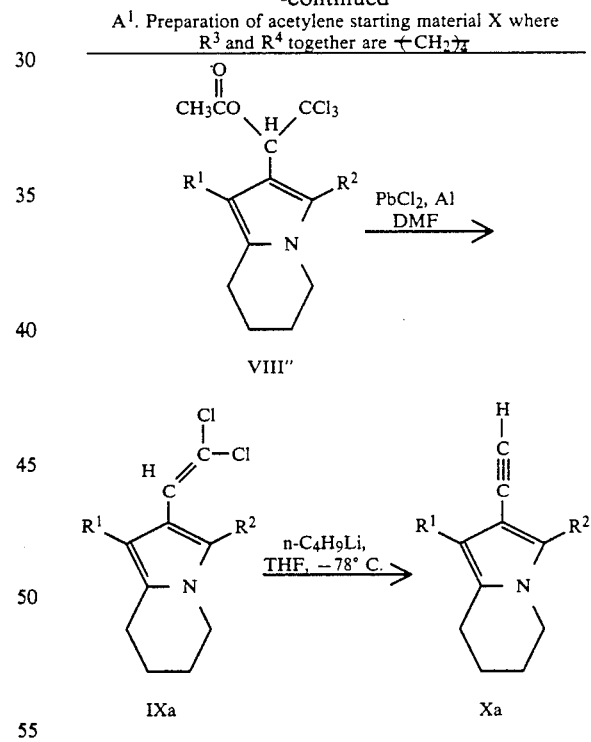
Reaction Sequence B.
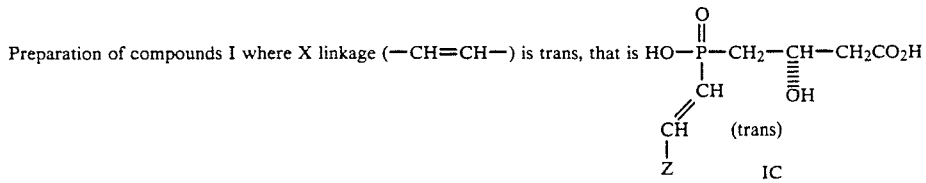

-continued
Reaction Sequence B.
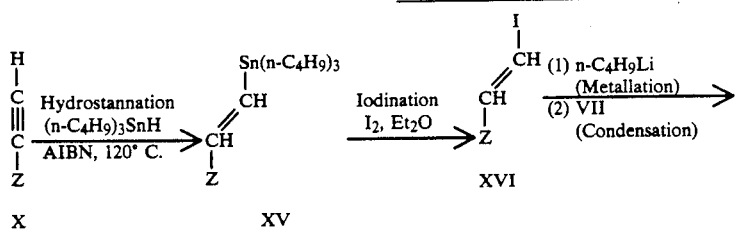
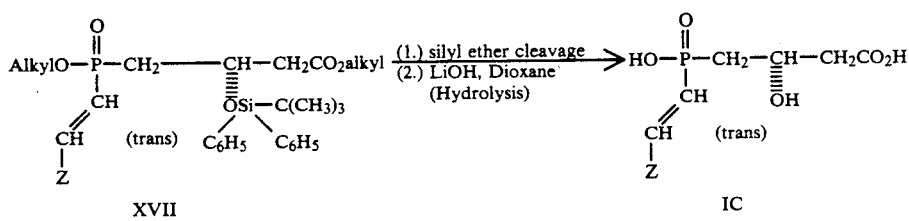
Reaction Sequence C.
Alternative Preparation of Compound I where X linkage (—CH=CH—) is trans, that is, compound IC.
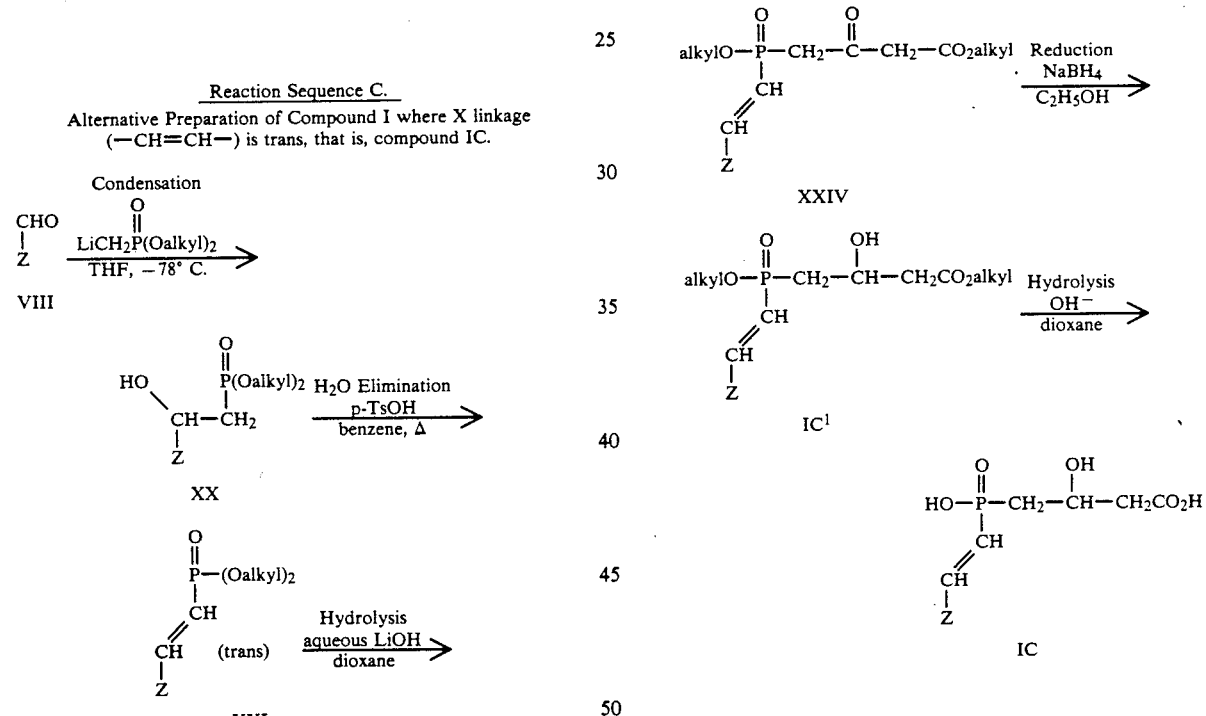
-continued
Reaction Sequence C.
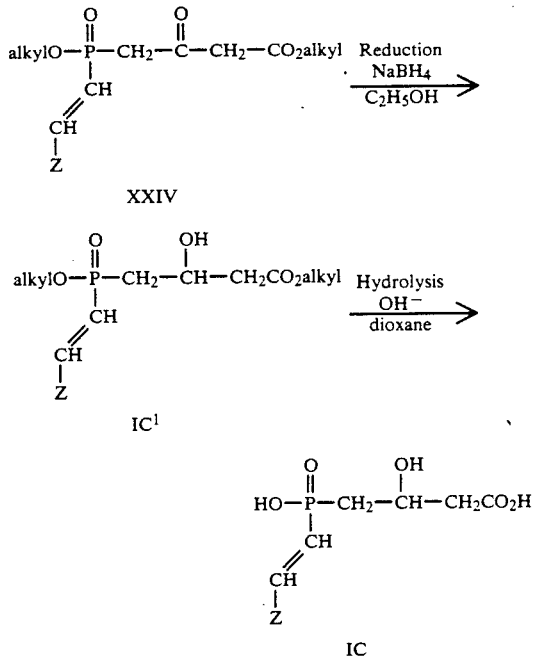
Reaction Sequence D.
Preparation of Compounds of Formula I where X is —CH$_2$—, —CH$_2$CH$_2$— or —CH$_2$CH$_2$CH$_2$—
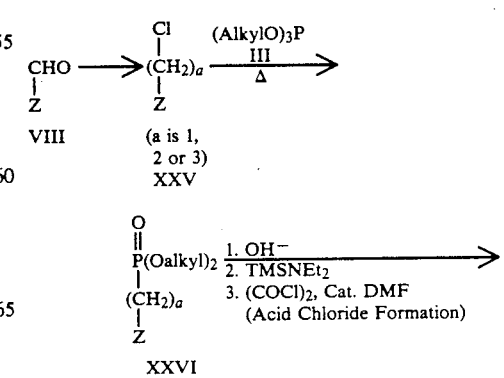

-continued
Reaction Sequence D.

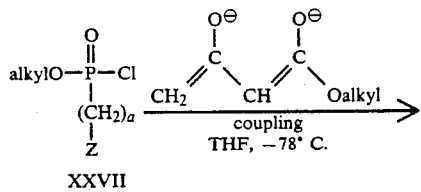

XXVII

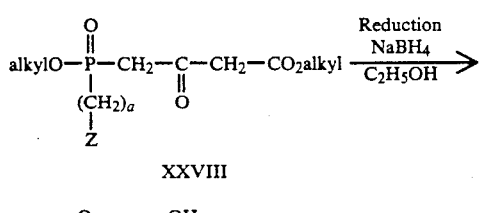

XXVIII

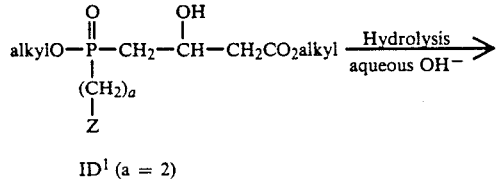

ID¹ (a = 2)
IE¹ (a = 1)
IF¹ (a = 3)

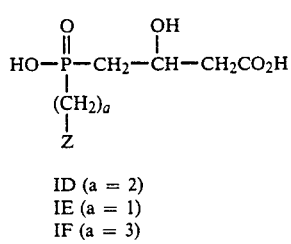

ID (a = 2)
IE (a = 1)
IF (a = 3)

As seen in the above Reaction Sequence "A", compounds of Formula I may be prepared by subjecting iodide A to an Arbuzov reaction by heating iodide A

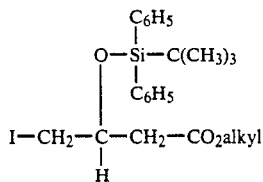

and phosphite III

    III employing standard Arbuzov conditions and procedures to form the phosphonate IV

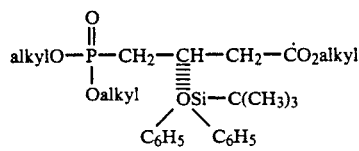

Phosphonate IV is then subjected to a phosphorus ester cleavage by treating a solution of phosphonate IV in an inert organic solvent, such as methylene chloride, sequentially with bis(trimethylsilyl)trifluoroacetamide (BSTFA) and trimethylsilyl bromide, under an inert atmosphere such as argon, to form the phosphonic acid V

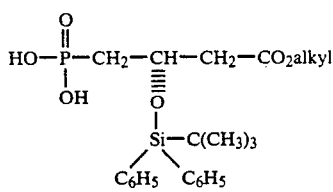

Phosphonic acid V is esterified by treating V in dry pyridine with a lower alkyl alcohol (such as methanol) and dicyclohexyl carbodiimide and the resulting reaction mixture is stirred under an inert atmosphere, such as argon, to form phosphonic monoalkyl ester VI. Phosphonic monoester VI is then dissolved in an inert organic solvent, such as, methylene chloride, benzene or tetrahydrofuran (THF) and treated with trimethylsilyl-diethylamine and stirred under an inert atmosphere such as argon, the mixture is evaporated and then dissolved in methylene chloride (or other appropriate inert organic solvent). The resulting solution is cooled to a temperature within the range of from about −10° C. to about 0° C., treated with oxalyl chloride and catalytic dimethylformamide and then evaporated to give crude phosphonochloridate VII. The phosphonochloridate VII is dissolved in inert organic solvent such as toluene, diethyl ether or THF, the solution is cooled to a temperature within the range of from about −90° C. to about 0° C. and preferably from about −85° C. to about −30° C. and treated with a cooled (same range as solution of phosphonochloridate VII) solution of the lithium anion of acetylene X formed by treating with a lithium source such as n-butyllithium in hexane or other inert solvent,

employing a molar ratio of VII:X of within the range of from about 3:1 to about 1:1 and preferably from about 1.5:1 to about 2:1 to form the acetylenic phosphinate XI

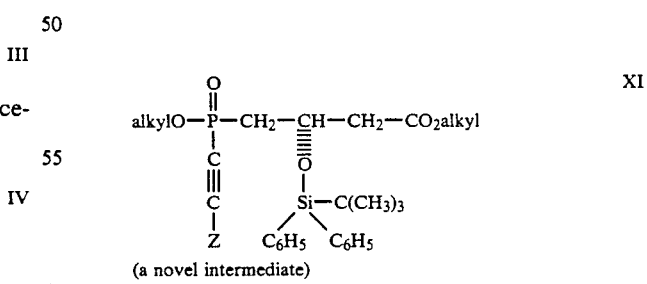

(a novel intermediate)

Acetylenic phosphinate XI may then be employed to prepare the various compounds of the present invention as follows. Acetylenic phosphnate XI is converted to acetylenic phosphinate IA¹ by subjecting XI to silyl ether cleavage by treating XI in an inert organic solvent such as tetrahydrofuran, with glacial acetic acid and tetrabutylammonium fluoride to form ester IA¹

$$\underset{\text{IA}^1}{\text{alkylO}-\overset{\overset{O}{\|}}{\underset{\underset{\underset{Z}{|}}{\underset{C}{\|}}}{P}}-CH_2-\overset{\equiv}{\underset{OH}{CH}}-CH_2-CO_2\text{alkyl}}$$

which may then be hydrolyzed to the corresponding basic salt or acid, that is, where $R^x$ is $R^{xa}$ which is ammonium, alkali metal, alkaline earth metal, an amine and the like, by treatment with strong base such as lithium hydroxide in the presence of dioxane, tetrahydrofuran or other inert organic solvent under an inert atmosphere such as argon, at 25° C., employing a molar ratio of base:ester $IA^1$ of within the range of from about 1:1 to about 1.1:1 to form the corresponding basic salt $$\underset{\text{IA}^2}{\text{alkylO}-\overset{\overset{O}{\|}}{\underset{\underset{\underset{Z}{|}}{\underset{C}{\|}}}{P}}-CH_2-\overset{\equiv}{\underset{OH}{CH}}-CH_2-CO_2-R^{xa}}$$

Compound $IA^2$ may then be treated with strong acid such as HCl to form the corresponding acid $IA^3$ $$\underset{\text{IA}^3}{\text{alkylO}-\overset{\overset{O}{\|}}{\underset{\underset{\underset{Z}{|}}{\underset{C}{\|}}}{P}}-CH_2-\overset{\equiv}{\underset{OH}{CH}}-CH_2-CO_2H}$$

The ester $IA^1$ may be converted to the corresponding di-basic salt by treating ester $IA^1$ with strong base at 50°-60° C. employing a molar ratio of base:ester $IA^1$ of within the range of from about 2:1 to about 4:1 to form $IA^4$ $$\underset{\text{IA}^4}{R^{xa}O-\overset{\overset{O}{\|}}{\underset{\underset{\underset{Z}{|}}{\underset{C}{\|}}}{P}}-CH_2-\overset{\equiv}{\underset{OH}{CH}}-CH_2-CO_2R^{xa}}$$

The dibasic salt $IA^4$ may be converted to the corresponding acid by treatment with strong acid such as HCl to form acid IA.

Phosphinate compounds of the invention where X is (cis) —CH=CH—, that is, IB are formed by subjecting acetylenic phosphinate XI to selective reduction, for example by treating XI with $H_2$ in the presence of a reduction catalyst such as palladium on carbon, palladium on barium carbonate and an inert organic solvent such as methanol to form the silyl ether XII $$\underset{\text{XII}}{\text{alkylO}-\overset{\overset{O}{\|}}{\underset{\underset{\underset{Z}{|}}{\underset{CH}{\|}}}{\underset{CH}{|}}}{P}}-CH_2-\underset{\underset{\underset{C_6H_5}{}}{\overset{O}{|}}}{\underset{\underset{Si-C(CH_3)_3}{}}{CH}}-CH_2CO_2\text{-alkyl}$$

(a novel intermediate)

Silyl ether XII may then be subjected to silyl ether cleavage and hydrolysis as described above to form the ester $IB^1$ $$\underset{\text{IB}^1}{\text{alkylO}-\overset{\overset{O}{\|}}{\underset{\underset{\underset{Z}{|}}{\underset{CH}{\|}}}{\underset{(cis)\ CH}{|}}}{P}}-CH_2-\overset{\equiv}{\underset{OH}{CH}}-CH_2-CO_2\text{-alkyl},$$

the basic salt $IB^2$ $$\underset{\text{IB}^2}{\text{alkylO}-\overset{\overset{O}{\|}}{\underset{\underset{\underset{Z}{|}}{\underset{CH}{\|}}}{\underset{(cis)\ CH}{|}}}{P}}-CH_2-\overset{\equiv}{\underset{OH}{CH}}-CH_2-CO_2R^{xa},$$

the acid $IB^3$ $$\underset{\text{IB}^3}{\text{alkylO}-\overset{\overset{O}{\|}}{\underset{\underset{\underset{Z}{|}}{\underset{CH}{\|}}}{\underset{(cis)\ CH}{|}}}{P}}-CH_2-\overset{\equiv}{\underset{OH}{CH}}-CH_2-CO_2H$$

the dibasic metal salt $IB^4$ $$\underset{\text{IB}^4}{R^{xa}O-\overset{\overset{O}{\|}}{\underset{\underset{\underset{Z}{|}}{\underset{CH}{\|}}}{\underset{(cis)\ CH}{|}}}{P}}-CH_2-\overset{\equiv}{\underset{OH}{CH}}-CH_2-CO_2R^{xa}$$

and the corresponding diacid IB.

Phosphinate compounds of the invention where X is —$CH_2$—$CH_2$—, that is, ID are formed by subjecting acetylenic phosphinate XII to catalytic reduction, for example by treating XII with $H_2$ in the presence of a reduction catalyst such as palladium on carbon and an inert organic solvent such as methanol at 50 psi to form the silyl ether XIII $$\underset{\text{XIII}}{\text{alkylO}-\overset{\overset{O}{\|}}{\underset{\underset{\underset{Z}{|}}{\underset{CH_2}{|}}}{\underset{CH_2}{|}}}{P}}-CH_2-\underset{\underset{\underset{C_6H_5}{}}{\overset{O}{|}}}{\underset{\underset{Si-C(CH_3)_3}{}}{CH}}-CH_2CO_2\text{-alkyl}$$

-continued
(a novel intermediate)

Silyl ether XII may then be subjected to silyl ether cleavage and hydrolysis as described above to form the ester ID¹

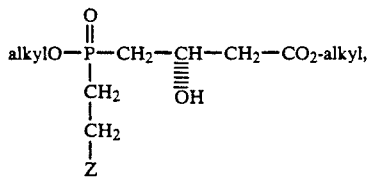  ID¹ the basic salt ID²

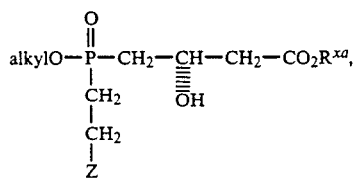  ID² the acid ID³

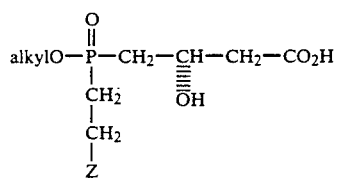  ID³ the dibasic salt ID⁴

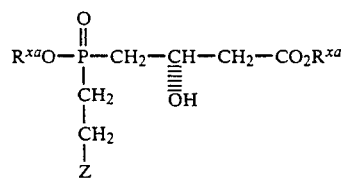  ID⁴ and the corresponding diacid ID.

Referring now to Reaction Sequence "B", compounds of Formula I wherein the X linking group between the phosphorus atom and the hydrophobic anchor Z is (trans) —CH=CH— may be prepared by treating a mixture of acetylene X and (n-C₄H₉)₃SnH with a radical initiator such as azobisisobutyrylnitrile (AIBN), hydrogen peroxide, benzoyl peroxide and the like, and heating the resulting solution to a temperature of within the range of from about 100° to about 140° C. under an inert atmosphere such as argon to form the vinyl stannane XV

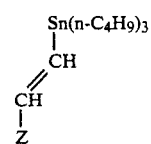  XV

Vinyl stannane XV dissolved in an organic solvent such as ethyl ether, methylene chloride or chloroform is treated with iodine and stirred under an inert atmosphere such as argon to form vinyl iodide XVI

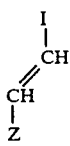  XVI

A cooled solution of vinyl iodide XVI (−78° to 40° C.) in dry organic solvent such as tetrahydrofuran, or ethyl ether is treated with a metallating agent such as n-butyllithium in an inert organic solvent such as hexane and the mixture is cooled at a temperature of from −78° to −40° C. under an inert atmosphere such as argon. The anion is added to a cooled (−78° to −40° C.) solution of phosphonochloridate VII at a molar ratio of XVI:VII of within the range of from about 1:1 to about 2:1 and preferably from about 1:1 to about 1.5:1 in dry inert organic solvent such as tetrahydrofuran, or ethyl ether to form the silyl ether XVII

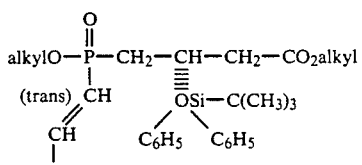  XVII (a novel intermediate)

The silyl ether XVII is subjected to silyl ether cleavage by treating a solution of XVII in an inert organic solvent such as tetrahydrofuran, or acetonitrile with glacial acetic acid and a solution of (n-C₄H₉)₄NF in an inert organic solvent such as tetrahydrofuran to form the hydroxy diester IC¹

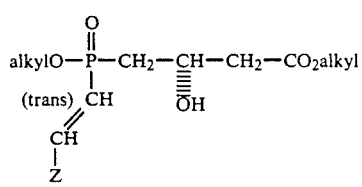  IC¹

Diester IC¹ may then be hydrolyzed as described above to form the basic salt IC²,

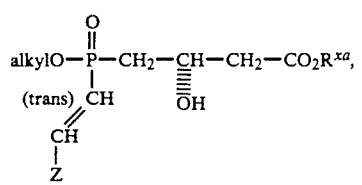  IC² the acid IC³

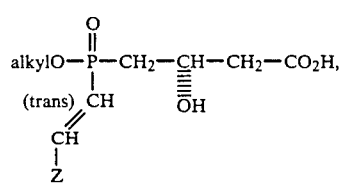  IC³ the dibasic salt IC⁴

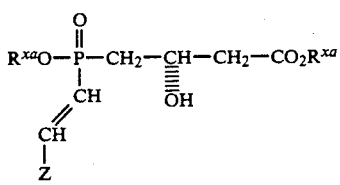

and the corresponding diacid IC

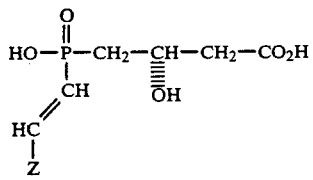

In an alternative process, as shown in Reaction Sequence "C", compounds of Formula I wherein the X linking group between the phosphorus atom and the hydrophobic anchor Z is (trans)—CH=CH— may be prepared by subjecting aldehyde VIII

CHO
|
Z
          VIII to a condensation reaction with a cooled (−90° to 0° C.) solution of dialkyl methylphosphonate and butyl lithium (LiCH$_2$PO(alkyl)$_2$) in the presence of an organic solvent such as tetrahydrofuran or ethyl ether to form the β-hydroxyphosphonate XX

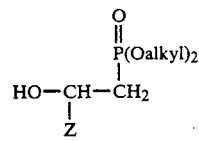

The β-hydrophosphonate XX is then treated with p-toluenesulfonic acid in the presence of benzene or toluene while heating to a temperature within the range of from about 50° to about 120° C., preferably at reflux, to eliminate water and form the trans-olefin XXI

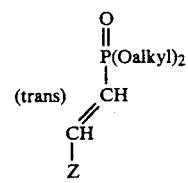

which is hydrolyzed by treating with aqueous alkali metal hydroxide, such as LiOH, in the presence of dioxane or other inert organic solvent and then with acid such as hydrochloric acid to form the monoacid ester XXII

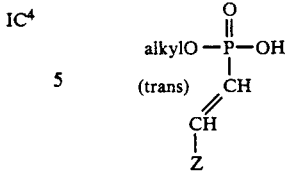

A solution of the monoacid ester XXII in dry methylene chloride is treated with trimethylsilyldiethylamine. The mixture is evaporated and the resulting oil is taken up in dry methylene chloride cooled to 0° and treated with oxalyl chloride and a catalytic amount of dimethyl formamide under an inert atmosphere such as argon to form phosphonochloridate XXIII

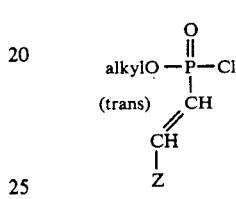

Phosphonochloridate XXIII is condensed with an alkyl acetoacetate dianion such as methyl acetoacetate dianion in the presence of an inert organic solvent such as tetrahydrofuran at reduced temperature of −90° to −40° C. employing a molar ratio of phosphonochloridate:dianion of within the range of from about 1:1 to about 0.75:1 to form the ketophosphonate XXIV

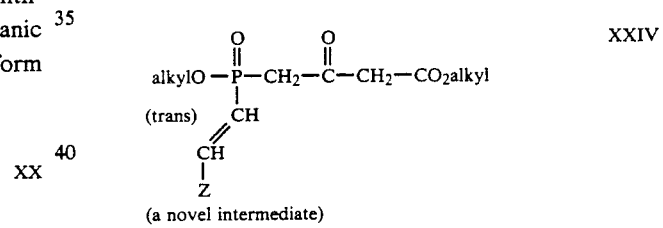

(a novel intermediate)

which is reduced by treatment with a reducing agent such as sodium borohydride in the presence of an alkanol such as ethanol to form the phosphinate IC$^1$

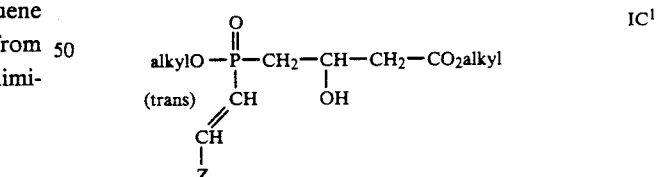

Diester IC$^1$ may then be hydrolyzed as described above to form the basic salt IC$^2$,

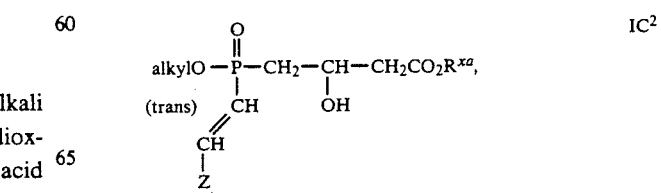

the acid IC$^3$

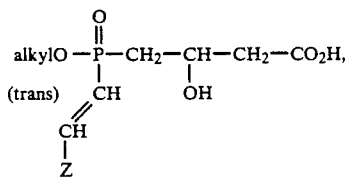

the basic salt IC⁴

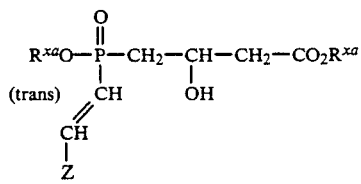

and the corresponding diacid IC.

Referring to Reaction Sequence D, compounds of Formula I wherein X is —(CH₂)$_a$— and a is 1, 2 or 3, that is —CH₂—, —CH₂CH₂— or —CH₂CH₂CH₂— may be prepared starting with aldehyde VIII which is converted to halide VIIIa using conventional procedures. For example, the aldehyde VIII may be reduced with NaBH₄ in the presence of ethanol to form the corresponding alcohol $$\begin{array}{c} CH_2OH \\ | \\ Z \end{array} \quad \text{VIIIa}$$

which is treated with mesyl chloride in the presence of an organic base such as triethylamine and a solvent such as methylene chloride to form the chloride XXV (a=1).

The chloride XXV is subjected to a condensation reaction where XXV is treated with phosphite III employing a molar ratio of III:XXV of within the range of from about 1:1 to about 10:1 and a temperature within the range of from about 100° to about 150° C. to form phosphonate diester XXVI. A solution of the phosphonate diester XXVI in a solvent such as dioxane is treated with a strong base such as an alkali metal hydroxide, for example, LiOH, to form a corresponding monoester which is treated with oxalyl chloride in the presence of an inert organic solvent such as dimethylformamide to form the corresponding phosphonochloridate XXVII. XXVII is condensed with an alkyl acetoacetate dianion such as methylacetoacetate dianion in the presence of an inert organic solvent such as tetrahydrofuran at reduced temperatures of from about −90° to about −40° C. employing a molar ratio of phosphonochloridate XXVII:dianion of within the range of from about 1:1 to 0.75:1 to form the ketophosphinate XXVIII which is a novel intermediate. Ketophosphinate XXVIII may then be reduced to the corresponding phosphinate ID¹, IE¹ and IF¹ which may be hydrolyzed to form the corresponding diacids ID, IE and IF following procedures as described with respect to Reaction Sequence C.

The acetylene starting material X (where R³ and R⁴ together form —(—CH=CH—)₂) may be prepared from the corresponding aldehyde VIII $$\begin{array}{c} CHO \\ | \\ Z \end{array} \quad \text{VIII}$$

by subjecting VIII to a Wittig reaction, for example, by treating a cooled solution of VIII (−25° C. to 0° C.) in triphenylphosphine, and an inert organic solvent such as methylene chloride, with a solution of tetrabromomethane (CBr₄) in an inert organic solvent such as methylene chloride to form vinyl dibromide IX $$\begin{array}{c} CH=CBr_2 \\ | \\ Z \end{array} \quad \text{IX}$$

Compound IX is subjected to dehydrohalogenation by treatment with n-butyllithium in an inert organic solvent such as hexane under an inert atmosphere to give X.

Alternatively, aldehyde VIII may be converted directly to acetylene X by treatment with dimethyl diazomethylphosphonate in the presence of potassium t-butoxide in an inert solvent such as tetrahydrofuran (−78° C. to 25° C.) under an inert atmosphere.

Where R³ and R⁴ together form —(CH₂)₄—, as seen in Reaction Sequence A', starting material Xa may be prepared by treating a solution of aldehyde VIII' and chloroform in dry inert organic solvent such as tetrahydrofuran (THF) at a reduced temperature of within the range of from about −80° to about −50° C. under an inert atmosphere such as argon, with a solution of lithium bis(trimethylsilyl)amide in an inert organic solvent such as THF or employing a molar ratio of aldehyde VIII':lithium bis(trimethylsilyl)amide of within the range of from about 0.9:1 to about 1:1.

The reaction product VIII'a is treated with acetic anhydride in the presence of pyridine, to form compound VIII". A solution of VIII" in dimethylformamide under an inert atmosphere such as argon, is treated with PbCl₂ and aluminum foil cut into small pieces employing a molar ratio of VIII":PbCl₂ of within the range of from about 1:01 to about 1:0.2 and a molar ratio of PbCl₂:Al of within the range of from about 1:1 to about 1:1.2, to form IXa. Compound IXa is then treated with a lithium source such as n-butyllithium in an inert organic solvent such as THF or hexane at a temperature withing the range of from about −80° to about −50° C. to form acetylene Xa. Acetylene Xa may be employed in place of X in the reactions described herein.

The above represents a novel method for preparing acetylene compounds of structure Xa.

The iodide starting material A may be prepared starting with the bromide C $$\begin{array}{c} OH \\ | \\ Br-CH_2-CH-CH_2CO_2alkyl \end{array} \quad C$$

(which is prepared by employing procedures as described in Tetrahedron Lett. 26, 2951 (1985)). which is dissolved in solution in dimethylformamide (DMF) with imidazole and 4-dimethylamino pyridine and the resulting solution is treated with t-butyldiphenyl silyl chloride under an inert atmosphere such as argon to form the silyl ether D $$\begin{array}{c} C_6H_5 \quad C_6H_5 \\ \diagdown \diagup \\ OSi-C(CH_3)_3 \\ | \\ Br-CH_2-CH-CH_2CO_2alkyl \end{array} \quad D$$

A solution of silyl ether D in an inert organic solvent such as methyl ethyl ketone or DMF is treated with sodium iodide under an inert atmosphere such as argon, to form iodide A.

The starting aldehyde compounds VIII, that is $$\underset{Z}{\overset{CHO}{|}} \qquad \text{VIII}$$

are known compounds.

The various intermediates XI, XII, XIII, XVII and XXIV also are part of the present invention. These novel intermediates may be represented by the following generic formula:

$$\text{alkylO}-\underset{\underset{Z}{\overset{|}{X}}}{\overset{\overset{O}{\|}}{P}}-CH_2-\underset{\overset{\|}{O}}{\overset{|}{C}}-CH_2-CO_2\text{alkyl} \qquad XXXV$$

wherein Z is as defined above, including all stereoisomers thereof.

The compounds of the invention may be prepared as racemic mixtures and may later be resolved to obtain the S-isomer which is preferred. However, the compounds of the invention may be prepared directly in the form of their S-isomers as described herein and in the working examples set out hereinafter.

The compounds of the invention are inhibitors of 3-hydroxy-3-methyl-glutaryl coenzyme A (HMG-CoA) reductase and thus are useful in inhibiting cholesterol biosynthesis as demonstrated by the following tests.

1) Rat Hepatic HMG-CoA Reductase

Rat hepatic HMG-CoA reductase activity is measured using a modification of the method described by Edwards (Edwards, P. A., et al., J. Lipid Res. 20:40, 1979). Rat hepatic microsomes are used as a source of enzyme, and the enzyme activity is determined by measuring the conversion of the $^{14}$C-HMG-CoA substrate to $^{14}$C-mevalonic acid.

a. Preparation of Microsomes

Livers are removed from 2–4 cholestyramine-fed, decapitated, Sprague Dawley rats, and homogenized in phosphate buffer A (potassium phosphate, 0.04 M, pH 7.2; KCl, 0.05 M; sucrose, 0.1 M; EDTA, 0.03 M; aprotinin, 500 KI units/ml). The homogenate is spun at 16,000 × g for 15 minutes at 4° C. The supernatant is removed and recentrifuged under the same conditions a second time. The second 16,000 × g supernatant is spun at 100,000 × g for 70 minutes at 4° C. Pelleted microsomes are resuspended in a minimum volume of buffer A (3–5 ml per liver), and homogenized in a glass/glass homogenizer. Dithiothreitol is added (10 mM), and the preparation is aliquoted, quick frozen in acetone/dry ice, and stored at −80° C. The specific activity of the first microsomal preparation was 0.68 nmole mevalonic acid/mg protein/minute.

b. Enzyme Assay

The reductase is assayed in 0.25 ml which contains the following components at the indicated final concentrations:

| | |
|---|---|
| 0.04M | Potassium phosphate, pH 7.0 |
| 0.05M | KCl |
| 0.10M | Sucrose |
| 0.03M | EDTA |
| 0.01M | Dithiothreitol |
| 3.5 mM | NaCl |
| 1% | Dimethylsulfoxide |
| 50–200 μg | Microsomal protein |
| 100 μM | $^{14}$C-[DL]HMG-CoA (0.05 μCi, 30–60 mCi/mmole) |
| 2.7 mM | NADPH (nicotinamide adenine dinucleotide phosphate) |

Reaction mixtures are incubated at 37° C. Under conditions described, enzyme activity increases linearly up to 300 μg microsomal protein per reaction mixture, and is linear with respect to incubation time up to 30 minutes. The standard incubation time chosen for drug studies is 20 minutes, which results in 12–15% conversion of HMG-CoA substrate to the mevalonic acid product. [DL-]HMG-CoA substrate is used at 100 μM, twice the concentration needed to saturate the enzyme under the conditions described. NADPH is used in excess at a level 2.7 times the concentration required to achieve maximum enzyme velocity.

Standardized assays for the evaluation of inhibitors are conducted according to the following procedure. Microsomal enzyme is incubated in the presence of NADPH at 37° C. for 15 minutes. DMSO vehicle with or without test compound is added, and the mixture further incubated for 15 minutes at 37° C. The enzyme assay is initiated by adding $^{14}$C-HMG-CoA substrate. After 20 minutes incubation at 37° C. the reaction is stopped by the addition of 25 μl of 33% KOH. $^{3}$H-mevalonic acid (0.05 μCi) is added, and the reaction mixture allowed to stand at room temperature for 30 minutes. Fifty μl 5N HCl is added to lactonize the mevalonic acid. Bromophenol blue is added as a pH indicator to monitor an adequate drop in pH. Lactonization is allowed to proceed for 30 minutes at room temperature. Reaction mixtures are centrifuged for 15 minutes at 2800 rpm. The supernatants are layered onto 2 grams AG 1-X8 anion exchange resin (Biorad, formate form) poured in 0.7 cm (id) glass columns, and eluted with 2.0 ml H$_2$O. The first 0.5 ml is discarded, and the next 1.5 ml is collected and counted for both tritium and carbon 14 in 10.0 ml Opti-fluor scintillation fluid. Results are calculated as nmoles mevalonic acid produced per 20 minutes, and are corrected to 100% recovery of tritium. Drug effects are expressed as I$_{50}$ values (concentration of drug producing 50% inhibition of enzyme activity) derived from composite dose response data with the 95% confidence interval indicated.

Conversion of drugs in lactone form to their sodium salts is accomplished by solubilizing the lactone in DMSO, adding a 10-fold molar excess of NaOH, and allowing the mixture to stand at room temperature for 15 minutes. The mixture is then partially neutralized (pH 7.5–8.0) using 1N HCl, and diluted into the enzyme reaction mixture.

2) Cholesterol Synthesis in Freshly Isolated Rat Hepatocytes

Compounds which demonstrate activity as inhibitors of HMG-CoA reductase are evaluated for their ability to inhibit $^{14}$C-acetate incorporation into cholesterol in freshly isolated rat hepatocyte suspensions using methods originally described by Capuzzi et al. (Capuzzi, D. M. and Margolis, S., Lipids, 6:602, 1971).

a. Isolation of Rat Hepatocytes

Sprague Dawley rats (180-220 grams) are anesthetized with Nembutol (50 mg/kg). The abdomen is opened and the first branch of the portal vein is tied closed. Heparin (100-200 units) is injected directly into the abdominal vena cava. A single closing suture is placed on the distal section of the portal vein, and the portal vein is canulated between the suture and the first branching vein. The liver is perfused at a rate of 20 ml/minute with prewarmed (37° C.), oxygenated buffer A (HBSS without calcium or magnesium containing 0.5 mM EDTA) after severing the vena cava to allow drainage of the effluent. The liver is additionally perfused with 200 ml of prewarmed buffer B (HBSS containing 0.05% bacterial collagenase). Following perfusion with buffer B, the liver is excised and decapsulated in 60 ml Waymouth's medium allowing free cells to disperse into the medium. Hepatocytes are isolated by low speed centrifugation for 3 minutes at 50× g at room temperature. Pelleted hepatocytes are washed once in Waymouth's medium, counted and assayed for viability by trypan blue exclusion. These hepatocyte enriched cell suspensions routinely show 70-90% viability.

b. $^{14}C$-Acetate Incorporation into Cholesterol

Hepatocytes are resuspended at $5 \times 10^6$ cells per 2.0 ml in incubation medium (IM) [0.02 M Tris-HCl (pH 7.4), 0.1 M KCl, 0.33 mM $MgCl_2$, 0.22 mM sodium citrate, 6.7 mM nicotinamide, 0.23 mM NADP, 1.7 mM glucose-6-phosphate].

Test compounds are routinely dissolved in DMSO or $DMSO:H_2O$ (1:3) and added to the IM. Final DMSO concentration in the IM is $\leq 1.0\%$, and has no significant effect on cholesterol synthesis.

Incubation is initiated by adding $^{14}C$-acetate (58 mCi/mmol, 2 $\mu$Ci/ml), and placing the cell suspensions (2.0 ml) in 35 mm tissue culture dishes, at 37° C. for 2.0 hours. Following incubation, cell suspensions are transferred to glass centrifuge tubes and spun at 50 × g for 3 minutes at room temperature. Cell pellets are resuspended and lysed in 1.0 ml $H_2O$, and placed in an ice bath.

Lipids are extracted essentially as described by Bligh, E. G. and W. J. Dyer, Can. J. Biochem. and Physiol., 37:911, 1959. The lower organic phase is removed and dried under a stream of nitrogen, and the residue resuspended in (100 $\mu$l) chloroform:methanol (2:1). The total sample is spotted on silica gel (LK6D) thin-layer plates and developed in hexane:ethyl ether:acetic acid (75:25:1). Plates are scanned and counted using a BioScan automated scanning system. Radiolabel in the cholesterol peak (RF 0.28) is determined and expressed at total counts per peak and as a percent of the label in the total lipid extract. Cholesterol peaks in control cultures routinely contain 800-1000 cpm, and are 9-20% of the label present in the total lipid extract; results compatable with Capuzzi, et al., indicating 9% of extracted label in cholesterol.

Drug effects (% inhibition of cholesterol synthesis) are determined by comparing % of label in cholesterol for control and drug treated cultures. Dose response curves are constructed from composite data from two or more studies, and results are expressed as $I_{50}$ values with a 95% confidence interval.

3) Cholesterol Synthesis in Human Skin Fibroblasts

Compound selectivity favoring greater inhibitory activity in hepatic tissue would be an attribute for a cholesterol synthesis inhibitor. Therefore, in addition to evaluating cholesterol synthesis inhibitors in hepatocytes, these compounds are also tested for their activity as inhibitors of cholesterol synthesis in cultured fibroblasts.

a. Human Skin Fibroblast Cultures

Human skin fibroblasts (passage 7-27) are grown in Eagles' minimal essential medium (EM) containing 10% fetal calf serum. For each experiment, stock cultures are trypsonized to disperse the cell monolayer, counted, and plated in 35 mm tissue culture wells ($5 \times 10^5$ cells/2.0 ml). Cultures are incubated for 18 hours at 37° C. in 5% $CO_2$/95% humidified room air. Cholesterol biosynthetic enzymes are induced by removing the serum containing medium, washing the cell monolayers, and adding 1.0 ml of EM containing 1.0% fatty acid free bovine serum albumin, and incubating the cultures an additional 24 hours.

b. $^{14}C$-Acetate Incorporation into Cholesterol

Induced fibroblast cultures are washed with $EMEM_{100}$ (Earle's minimal essential medium). Test compounds are dissolved in DMSO or DMSO:EM (1:3) (final DMSO concentration in cell cultures $\leq 1.0\%$), added to the cultures, and the cultures preincubated for 30 minutes at 37° C. in 5% $CO_2$/95% humidified room air. Following preincubation with drugs, [1-$^{14}C$]Na acetate (2.0 $\mu$Ci/ml, 58 mCi/mmole) is added, and the cultures reincubated for 4 hours. After incubation, the culture medium is removed, and the cell monolayer (200 $\mu$g cell protein per culture) is scraped into 1.0 ml of $H_2O$. Lipids in the lysed cell suspension are extracted into chloroform:methanol as described for hepatocyte suspensions. The organic phase is dried under nitrogen, and the residue resuspended in chloroform:methanol (2:1) (100 $\mu$l), and the total sample spotted on silica gel (LK6D) thin-layer plates, and analyzed as described for hepatocytes.

Inhibition of cholesterol synthesis is determined by comparing the percent of label in the cholesterol peak from control and drug-treated cultures. Results are expressed as $I_{50}$ values, and are derived from composite dose response curves from two or more experiments. A 95% confidence interval for the $I_{50}$ value is also calculated from the composite dose response curves.

A further aspect of the present invention is a pharmaceutical composition consisting of at least one of the compounds of formula I in association with a pharmaceutical vehicle or diluent. The pharmaceutical composition can be formulated employing conventional solid or liquid vehicles of diluents and pharmaceutical additives of a type appropriate to the mode of desired administration. The compounds can be administered by an oral route, for example, in the form of tablets, capsules, granules or powders, or they can be administered by a parenteral route in the form of injectable preparations, such dosage forms containing from 1 to 2000 mg of active compound per dosage, for use in the treatment. The dose to be administered depends on the unitary dose, the symptoms, and the age and the body weight of the patient.

The compounds of formula I may be administered in a similar manner as known compounds suggested for use in inhibiting cholesterol biosynthesis, such as lovastatin, in mammalian species such as humans, dogs, cats and the like. Thus, the compounds of the invention may be administered in an amount from about 4 to 2000 mg in a single dose or in the form of individual doses from 1 to 4 times per day, preferably 4 to 200 mg in divided dosages of 1 to 100 mg, suitably 0.5 to 50 mg 2 to 4 times daily or in sustained release form.

The following working Examples represent preferred embodiments of the present invention. Unless otherwise indicated, all temperatures are expressed in degrees Centigrade. Flash chromatography was performed on either Merck 60 or Whatmann LPS-I silica gel. Reverse phase chromatography was performed on CHP-20 MCI gel resin supplied by Mitsubishi, Ltd.

As used in the following Examples, the abbreviations "Et$_2$O", "EtOAc", "MeOH" and "EtOH" refer to ethyl ether, ethyl acetate, methanol and ethanol, respectively.

EXAMPLE 1

(S)-4-[[[1-(4-Fluorophenyl)-3-(1-methylethyl)indolizin-2-yl]ethynyl]methoxyphosphinyl]-3-hydroxybutanoic acid, methyl ester

A. 4-Methyl-3-oxo-2-(2-pyridinylmethylene)pentanoic acid, ethyl ester

To a solution of ethyl isobutyrylacetate (15.78 g, 99.7 mmol) and pyridine-2-carboxaldehyde (10.7 g, 99.9 mmol) in dry benzene (100 mL) at room temperature under argon was added acetic acid (0.30 mL, 5.2 mmol) and piperidine (0.80 mL, 8.1 mmol). After stirring at room temperature for 1 hour and at reflux for 3 hours, the cooled mixture was washed with water, saturated NaHCO$_3$ and saturated NaCl solutions, dried (Na$_2$SO$_4$) and concentrated in vacuo. The crude product was purified by flash chromatography on silica gel eluting with ethyl acetate (EtOAc)-hexane (1:9) to give title compound (20.61 g, 83%) as an orange, viscous oil which crystallized on standing to a semi-solid mass, mp 53°–55° C.

TLC (EtOAc-hexane; 1:1) R$_f$=0.39 and 0.33 (mixture of isomers).

B. β-(4-Fluorophenyl)-α-(2-methyl-1-oxopropyl)-2-pyridinepropanoic acid, ethyl ester To a solution of 2.0 M p-fluorophenylmagnesiumbromide-diethyl ether (Et$_2$O) (40.0 mL, 80.0 mmol) in dry tetrahydrofuran (THF) (300 mL) at 0° C. under argon was added cuprous iodide (0.84 g, 4.4 mmol). After stirring at 0° C. for 2–5 minutes, the mixture was cooled to −78° C. (bath temperature) and treated dropwise over 5 minutes with a solution of Part A compound (18.28 g, 74.0 mmol) in dry THF (100 mL). The resulting solution was allowed to warm to −50° C., maintained at −50° to −55° C. for 1 hour, treated with an additional portion of cuprous iodide (0.83 g) and slowly allowed to warm to −20° C. over 2 hours. The reaction was then quenched with saturated NH$_4$Cl solution (125 mL), the organic phase separated washed with saturated NH$_4$Cl, saturated NaHCO$_3$ and saturated NaCl solutions, dried (Na$_2$SO$_4$) and evaporated to dryness. The crude product (orange oil) was purified by flash chromatography on silica gel eluting with EtOAc-hexane (1:9) to give title compound (21.84 g, 86%) as an orange, viscous oil which crystallized on standing to a semi-solid mass, mp 106°–108° C.

TLC (EtOAc-hexane; 1:1) R$_f$=0.68 and 0.61 (mixture of isomers).

C. 1-(4-Fluorophenyl)-3-(1-methylethyl)-2-indolizinecarboxylic acid, ethyl ester To a solution of Part B compound (22.73 g, 69.9 mmol) in dry toluene (200 mL) at room temperature under argon was added trifluoroacetic anhydride (20 0 mL, 142 mmol) and the resulting mixture heated at 85°–90° C. (bath temperature) for 2 hours. The resulting light brown solution was evaporated to approximately half its original volume, diluted with EtOAc (100 mL) and carefully washed with saturated NaHCO$_3$ (3×100 mL) and saturated NaCl solutions, dried (Na$_2$SO$_4$) and evaporated to dryness. The residue was purified by flash chromatography on silica gel eluting with toluene-hexane (2:3 to 1:1) to give title compound (18.61 g, 86%) as a reddish oil. Trituration with cold hexane gave pure title compound (17.46 g 81%) as salmon-colored crystals, mp 99°–100° C.

TLC (EtOAc-hexane; 3:7) R$_f$=0.62.

Anal. Calc'd for C$_{20}$H$_{20}$NOF: C, 73.83; H, 6.20; N, 4.30; F, 5.84. Found: C, 33.52; H, 6.21; N, 4.16; F, 5.68.

D. 1-(4-Fluorophenyl)-3-(1-methylethyl)-2-indolizinemethanol

To a suspension of LiAIH$_4$ (2.50 g, 65.8 mmol) in dry THF 125 mL) at 0° C. under argon was added dropwise a solution of Part C compound (6.50 g, 20.0 mmol) in THF (50 mL). After stirring at 0° C. for 30 minutes and at room temperature for 2 hours, the mixture was again placed in an ice bath and treated succesively with H$_2$O (2.5 mL), 15% NaOH (2.5 mL) and H$_2$O (7.5 mL), then allowed to warm to room temperature. The resulting suspension was filtered through Celite and evaporated to dryness to give crude title compound (5.836 g) as a yellow foam. The crude product was crystallized from Et$_2$O-hexanes to give pure title compound (5.593 g, 99%) as yellow crystals, mp 90°–92° C.

TLC (EtOAc-hexane; 3:7) R$_f$=0.38.

E. 1-(4-Fluorophenyl)-3-(1-methylethyl)-2-indolizinecarboxaldehyde

To a solution of Part D compound (4.630 g, 16.36 mmol) in dry THF (100 mL) at 0° C. under argon was added dropwise via syringe 3.0 M methylmagnesium bromide-Et$_2$O (5.45 mL, 16.35 mmol). When the addition was complete, the mixture was allowed to warm to room temperature. After stirring at room temperature for 30 minutes, the resulting suspension was treated dropwise with a solution of 1,1'-(azodicarbonyl)-dipiperidine (4.395 g, 17.44 mmol) in dry THF (50 mL). After stirring at room temperature for 2 hours, the reaction was quenched with saturated NaCl solution (100 mL). The organic phase was separated, washed with saturated NaHCO$_3$ and saturated NACL solutions, dried (Na$_2$SO$_4$) and evaporated to dryness. The residue was taken up in Et$_2$O-hexane (1:1, 200 mL), filtered and the filtrate evaporated to a yellow foam. The crude product was purified by flash chromatography on silica gel eluting with Et$_2$O-hexane (3:100) to give title compound (4.127 g, 90%) as a yellow foam. The crude product was crystallized from cold hexane to give pure title compound (4.046 g, 88%) as yellow crystals, mp 94°–95° C.

TLC (EtOAc-hexane; 3:7) $R_f$=0.51.
Anal. Calc'd for $C_{18}H_{16}NOF$:
C, 76.85; H, 5.73; N, 4.98; F, 6.75. Found: C, 76.72; H, 5.73; N, 5.04; F, 6.64.

F.
2-(2,2-Dibromoethenyl)-2-(4-fluorophenyl)-3-(1-methylethyl)indolizine To a solution of Part E compound (3.890 g, 13.84 mmol) and triphenylphosphine (14.51 g, 55.4 mmol) in dry $CH_2Cl_2$ (100 mL) at $-30°$ to $-25°$ C. (bath temperature) under argon was added dropwise over 30 minutes a solution of carbon tetrabromide (9.18 g, 27.7 mmol) in $CH_2Cl_2$ (30 mL). After stirring at $-25°$ C. for an additional 1 hour, the mixture was treated with saturated $NaHCO_3$ solution (50 mL) and allowed to warm to room temperature. The organic phase was separated, dried ($Na_2SO_4$) and evaporated to dryness. The crude product was purified by flash chromatography on silica gel eluting with $CH_2Cl_2$-hexane (5:95) to give title compound (4.164 g, 69%) as a yellow semi-solid. The crude product was crystallized from hexane to give pure title compound (3.788 g, 63%) as pale yellow crystals, mp 134.5°–135° C.

TLC (EtOAc-hexane; 1:4) $R_f$=0.39.

G.
(S)-4-(Hydroxymethoxyphosphinyl)-3-[[(1,1-dimethylethyl)diphenylsilyl]oxy]-butanoic acid, methyl ester, dicyclohexylamine (1:1) salt (1) (S)-4-Bromo-3-hydroxybutanoic acid, methyl ester (1)(a) [R-(R*,R*)]-2,3,4-trihydroxybutanoic acid, calcium salt, hydrate Ref. Carbohydrate Research 72, pp. 301–304 (1979). Calcium carbonate (50 g) was added to a solution of D-isoascorbic acid (44.0 g, 250 mmol) in $H_2O$ (625 ml), the suspension cooled to 0° C. (ice bath) and treated portionwise with 30% $H_2O_2$ (100 ml). The mixture was stirred at 30°–40° C. (oil bath) for 30 minutes. Darco (10 g) was added and the black suspension heated on a steam bath until evolution of $O_2$ ceased. The suspension was filtered through Celite, evaporated in vacuo (bath temperature 40° C.). The residue was taken up in $H_2O$ (50 ml), warmed on a steam bath and $CH_3OH$ was added until the solution was turbid. The gummy precipitated solid was collected by filtration and air dried to give 30.836 g (75.2%) of desired calcium salt as a powdery white solid.

TLC (7:2:1) iPrOH—$NH_4OH$—$H_2O$, Rf=0.19, PMA.

(1)(b) [S-(R*,S*)]-2,4-Dibromo-3-hydroxybutanoic acid, methyl ester

Ref. Bock, K. et al., Acta Scandinavica (B) 37, pp 341–344 (1983)

Part (1)(a) calcium salt (30 g) was dissolved in 30–32% HBr in acetic acid (210 ml) and stirred at room temperature for 24 hours. Methanol (990 ml) was then added to the brown solution and it was stirred overnight. The mixture was evaporated to an orange oil, taken up in $CH_3OH$ (75 ml), refluxed for 2.0 hours and evaporated. The residue was partitioned between EtOAc (100 ml) and $H_2O$, the organic phase washed with $H_2O$ (2×) and brine then dried over anhydrous $Na_2SO_4$ and evaporated to give 22.83 g (90.5%) of crude dibromide as a light orange oil. TLC (1:1) EtOAc-Hex, Rf=0.69, UV & PMA.

(1)(c) (S)-4-Bromo-3-hydroxybutanoic acid, methyl ester

Ref. the same as for preparation of (1)(b).

An argon purged solution of the dibromide (20.80 g, 75.4 mmol) and anhydrous NaOAc (21.0 g) in EtOAc (370 ml) and glacial HOAc (37 ml) was treated with 5% Pd/C (1.30 g) and the black suspension stirred under of $H_2$ (1 atm) while monitoring $H_2$ uptake. After 2.0 hours $H_2$ uptake was complete, the mixture was filtered through Celite, the filtrate washed with saturated $NaHCO_3$ and brine then dried over anhydrous $MgSO_4$ and evaporated to give crude dibromoester as a brown oil. The crude oil was combined with another batch (starting from 36.77 g of the dibromide) and vacuum distilled to give 25.77 g (61.3%) of desired title bromoester as a colorless oil with b.p.=79°–80° C. (1.0 mm Hg). TLC (1:1) EtOAc-Hex, Rf=0.44, PMA.

Anal Calcd for $C_5H_9O_3Br$: C, 30.48; H, 4.60; Br, 40.56.

Found: C, 29.76; H, 4.50; Br, 39.86.

(2) (S)-4-Bromo-3-[[(1,1-dimethylethyl)diphenylsilyl]oxy]-butanoic acid, methyl ester A solution of part F(1) bromohydrin (4.0 g, 20.4 mmol), imidazole (6.94 g, 5.0 eq.), and 4-dimethylamino pyridine (4-DMAP) (12 mg, 0.005 eq.) in dry DMF (40 ml) was treated with t-butyldiphenylsilyl chloride (5.84 ml, 1.1 eq.) and the homogeneous mixture stirred overnight under argon at room temperature. The mixture was partitioned between 5% $KHSO_4$ and EtOAc, the organic phase washed with $H_2O$ and brine, dried over anhydrous $Na_2SO_4$ and evaporated to give 9.32 g (100%) of crude silyl ether as a colorless, viscous oil. TLC (3:1) Hex-EtOAc, Rf silyl ether=0.75, U.V. and PMA.

(3) (S)-4-Iodo-3-[[(1,1-dimethylethyl)diphenylsilyl]oxy]-butanoic acid, methyl ester A solution of the crude Part F(2) bromide (9.32 g, 201 mmole) in methyl ethyl ketone (60 ml, dried over 4 Å sieves) was treated with sodium iodide (15.06 g, 100.5 mmole, 5.0 eq.) and the yellow suspension refluxed for 5.0 hours under argon. The mixture was cooled, diluted with EtOAc, filtered, the filtrate washed with dilute $NaHSO_3$ (until colorless) and brine then dried over anhydrous $Na_2SO_4$ and evaporated in vacuo to give 10.17 g of a yellow oil. The crude oil was purified by flash chromatography on silica gel (600 g) eluting with (3:1) Hexane-$CH_2Cl_2$. Product fractions were combined and evaporated to give 7.691 g (74.2%, overall yield for both steps) of desired title iodide as a clear, colorless, viscous oil. TLC (3:1) Hex-EtOAc, product. Rf=0.75, U.V. and PMA. (Note: product iodide co-spots with starting bromide).

(4) (S)-4-Diisopropyloxyphosphinyl)-3-[[(1,1-dimethylethyl)diphenylsilyl]oxy]-butanoic acid, methyl ester Part (3) iodide (45.1 mmol., 21.70 g) was stirred under high vacuum for 30 minutes. Freshly distilled triisopropyl phosphite (0.451 mol., 93.92 g, 113.37 ml.) was added in one portion and the reaction mixture was stirred under argon and heated in a 155° C. oil bath for 16.5 hours. The mixture was then cooled to room temperature. Excess triisopropyl phosphite and volatile reaction products were removed by short path distillation (10 mm Hg) followed by Kugelrohr distillation (0.50 mm Hg, 100° C., 8 hours). The product was further purified via flash chromatography (95 mm diam. column, 6"/Merck silica gel, 6/3/1 Hexane/acetone/-toluene eluent, 2"/min flow rate, 50 ml fractions) to afford 17.68 g (33.96 mmol, 75% yield) of the title isopropylphosphonate as a clear viscous oil.

TLC: Silica gel $R_f=0.32$ (6:3:1 Hexane/acetone toluene)

$^1$HNMR: (270 MH$_z$, CDCl$_3$): $\delta$7.70–7.65 (m,4H), 7.45–7.35 (m,6H), 4.57–4.44 (m,3H), 3.59 (s,3H), 2.94 and 2.88 (2xd, 1H J=3.7 Hz), 2.65 and 2.60 (2xd, 1H J=7.4 Hz), 20 2.24–1.87 (Series of m, 2H), 1.19 and 1.12 (2xd, 12H J=6.3 Hz), 1.01 (s, 9H).

(5)
(S)-4-(Hydroxymethoxyphosphinyl)-3-[[(1,1-dimethylethyl)diphenylsilyl]oxy]butanoic acid, methyl ester, dicyclohexylamine (1:1) salt The Part (4) isopropyl phosphonate (30.5 mmol, 10.66 g) was stirred under argon, at room temperature, in 80 ml of dry CH$_2$Cl$_2$. This solution was treated dropwise (5 min) with bistrimethylsilyltrifluoroacetamide (BSTFA) (32.8 mmol, 8.44 g, 8.71 ml), followed by dropwise addition (10 min) of trimethylsilylbromide (TMSBr) (51.3 mmol, 7.84 g, 6.75 ml). After stirring at room temperature for 20 hours, the reaction mixture was quenched with 200 ml of 5% aqueous KHSO$_4$ and stirred vigorously for 15 minutes. The aqueous layer was extracted 3 times with ethylacetate. The organic extracts were combined, washed once with brine, dried over Na$_2$SO$_4$ and concentrated in vacuo. The residue was azeotroped 2 times with 50 ml of toluene. The precipitate which formed was suspended in toluene and filtered. The filtrate was concentrated and the azeotrope/filter process repeated. The resulting filtrate was evaporated in vacuo and then pumped under high vacuum for 5 hours. The resulting viscous clear oil was stirred under argon, at room temperature, in 50 ml of dry pyridine. This solution was treated in one portion with dicyclohexylcarbodiimide (DCC) (22.6 mmol, 4.65 g), followed by addition of methanol (41.0 mmol, 1.31 g, 1.67 ml). After stirring at room temperature for 20 hours, the reaction mixture was filtered through a celite pad in a sintered glass funnel. The celite was washed with ethyl acetate and the combined filtrates were evaporated in vacuo. The residue was redissolved in ethyl acetate and washed 2 times with 5% aqueous KHSO$_4$ and once with brine. The organic extract was dried over Na$_2$SO$_4$, filtered, the filtrate concentrated and azeotroped 2 times with toluene, suspended in toluene and filtered. The resulting filtrate was again concentrated, azeotroped, filtered and the filtrate evaporated in vacuo and placed under high vacuum for 6 hours to afford the phosphonate monoester as a clear viscous oil (10.2 g, >100% yield). TLC: silica gel $R_f=0.50$ (7:2:1 nPrOH/NH$_4$OH/H$_2$O). The phosphonate monoester [1.21 g was pumped under high vacuum for 4 hours, affording 1.16 g (2.57 mmol)] was dissolved in 10 ml of dry ethyl ether and treated dropwise with dicyclohexylamine (2.65 mmol, 0.481 g, 0.528 ml). The resulting homogeneous solution sat at room temperature for 7 hours resulting in significant crystal formation. The mixture was stored at −20° C. for 16 hours and then warmed to room temperature and filtered. The crystals were washed with cold, dry ethyl ether and then pumped under high vacuum over P$_2$O$_5$ for 18 hours. The crystals were subsequently pumped under high vacuum at 45° C. for 4 hours, affording 1.25 g (1.98 mmol, 77% yield) of the title dicyclohexylamine salt as a white powdery solid, m.p. 155°–156° C.

TLC: Silica gel $R_f=0.57$ (20% MeOH/CH$_2$Cl$_2$). $^1$H NMR: (270 MHz$_2$, CDCl$_3$): $\delta$ 7.71–7.65 (m, 4H), 7.40–7.32 (m, 6H), 4.02 (m, 1H), 3.52 (s, 3H), 3.28 and 3.22 (m, 1H), 3.11 (d, 3H J=11 Hz), 2.77–2.64 (m, 2H), 2.62–2.56 (m, 1H), 1.92–1.08 (Series of m, 22H), 1.00 (S, 9H).

Mass Spec: (FAB) 632 (M&H)$^+$
IR:(KBr) 3466–3457 (broad) 3046, 3016, 2997, 2937, 2858, 2836, 2798, 2721, 2704, 2633, 2533, 2447, 1736, 1449, 1435, 1426, 1379, 1243, 1231, 1191, 1107, 1074, 1061, 1051, 820 CM-1

Anal Calcd for C$_{22}$H$_{31}$ $_{o6}$PSi.C$_{12}$H$_{23}$N: C, 64.63; H, 8.61; N,2.22. Found: C, 64.51; H, 8.49; N, 2.18.

H.
(S)-4-(Chloromethoxyphosphinyl)-3-[[(1,1-dimethylethyl)diphenylsilyl]oxy]butanoic acid, methyl ester Part G salt (3.028 g, 4.80 mmol) was partitioned between EtOAc-5% KHSO$_4$ (100 mL each). The organic phase was washed with 5% KHSO$_4$ (4×50 mL) and saturated NaCl solutions, dried (Na$_2$SO$_4$) and evaporated to a colorless viscous oil. The free acid was taken up in dry CH$_2$Cl$_2$ (15 mL) and treated with trimethylsilyldiethylamine (1.85 mL, 9.77 mmole). After stirring at room temperature under argon for 1.5 hours, the mixture was evaportaed to dryness, taken up in dry benzene (10 mL) and again evaportaed to dryness. The crude silyl ester was taken up in CH$_2$Cl$_2$ (15 mL), placed in an ice bath under argon and treated with oxalyl chloride (0.45 mL, 5.16 mmole) and DMF (1 drop). After stirring at 0° C. for 15 minutes and at room temperature for 1 hour, the mixture was evaporated to dryness. The residue was taken up in benzene (15 mL), filtered through sinctered glass and evaporated to dryness to give crude title compound (ca. 4.80 mmol) as a pale yellow, viscous oil.

I.
(S)-3-[[(1,1-Dimethylethyl)diphenylsilyl]oxy]-4-[[1-(4-fluorophenyl)-3-(1-methylethyl)-2-indolizinyl]ethynyl]-methoxyphosphinylbutanoic acid, methyl ester To a solution of 1.6 M n-C$_4$H$_9$Li-hexane (3.85 mL, 6.16 mL) in dry THF (10 mL) at −78° C. under argon was added dropwise a solution of Part F compound (1.311 g, 3.00 mmol) in THF (10 mL) over 15 minutes. After stirring at −78° C. for 1 hour, the anion solution was transferred via cannula to a −78° C. solution of Part H compound (ca. 4.80 mmol) in dry THF (15 mL). After stirring at −78° C. for 1 hour, the reaction was quenched by the dropwise addition of saturated NH$_4$Cl (10 mL) and allowed to warm to room temperature. The mixture was made basic with saturated NaHCO$_3$ solution and extracted with EtOAc. The extracts were washed with saturated NaHCO$_3$ and saturated NaCl solutions, dried (Na$_2$SO$_4$) and evaporated to dryness. The crude product was purified by flash chromatography on silica gel eluting with EtOAc-hexane (2:3) to give title compound (1.943 g, 91% based on Part F compound) as a yellow foam.

TLC (acetone-hexane; 1:1) $R_f=0.51$.

J.
(S)-4-[[[1-(4-Fluorophenyl)-3-(1-methylethyl)indolizin-2-yl]ethynyl]methoxyphosphinyl]-3-hydroxybutanoic acid, methyl ester To a solution of Part I compound (1.817 g, 2.56 mmol) in dry THF (10 mL) at room temperature under argon was added glacial acetic acid (0.59 mL, 10.3 mmol) and a 1.0 M solution of (n-$C_4H_9$)$_4$NF in THF (7.70 mL, 7.70 mmol). After stirring at room temperature for 40 hours, the mixture was diluted with EtOAc (50 mL) washed successively with 1N HCl (3×50 mL) and saturated NaCl solutions, dried ($Na_2SO_4$) and evaporated to dryness. The residue was taken up in $CH_2Cl_2$ (8 mL)-$Et_2O$ (25 mL), cooled in an ice bath and treated with excess etheral diazomethane. The residue obtained by evaporation of the ether was purified by flash chromatography on silica gel eluting with acetonehexane (35:65) to give title ester (1.126 g, 93%) as a yellow glass.

TLC (acetone-hexane; 1:1) $R_f$=0.28.

EXAMPLE 2

(S)-4-[[[1-(4-Fluorophenyl)-3-(1-methylethyl)indolizin-2-yl]ethynyl]hydroxyphosphinyl]-3-hydroxybutanoic acid, dilithium salt To a solution of Example 1 ester (0.505 g, 1.07 mmol) in dioxane (6 mL) at room temperature under argon was added 1N LiOH solution (3.2 mL, 3.2 mmol). After stirring at room temperature for 3 hours, the mixture was evaporated to dryness. The crude product was purified on CHP-20 (20 mL bed volume, 1 inch diameter) eluting with water (300 mL) followed by $CH_3OH$-water (50:50; 300 mL). The product containing fractions were combined and evaporated to dryness. The solid residue was triturated with water-acetonitrile to give pure title salt (0.464 g, 90%) as a pale yellow solid, mp 287°-288° C. (d). $[\alpha]_D$= +4.5° (c=0.57, $CH_3OH$).

TLC (i-$C_3H_7OH$-concentrated $NH_4OH$-$H_2O$; 7:2:1) $R_f$=0.52.

Anal. Calc'd for 1.5 mole $H_2O$: C, 57.28; H, 5.02; N, 2.91; F, 3.94; P, 6.42. Found: C, 57.32; H, 5.09; N, 2.98; F, 3.77; P, 6.23.

EXAMPLE 3

(S)-4-[[[3-(4-Fluorophenyl)-1-(1-methylethyl)-2-indolizinyl]ethynyl]methoxyphosphinyl]-3-hydroxybutanoic acid, methyl ester A. 3-(4'-Fluorophenyl)-3-oxopropanoic acid, ethyl ester To a suspension of sodium hydride (29.5 g of 60% oil dispersion, washed free of oil with hexane) in diethyl carbonate (88 mL, 0.726 mol) at room temperature under argon was added dropwise over 30 minutes p-fluoroacetophenone (50.0 g, 0.362 mol). Ethanol (0.1 mL) was added during the addition to initiate the reaction. After ⅓ of the ketone had been added, white solid had separated and $Et_2O$ (600 mL) was added to facilitate stirring. When the addition was complete the mixture was refluxed for 3 hours. The mixture was then placed in an ice bath, and the reaction was quenched by the dropwise addition of water (100 mL) and 5% $KHSO_4$ solution (100 mL). The mixture was acidified with 10% $H_2SO_4$, the organic phase separated and washed with saturated $NaHCO_3$ and saturated NaCl solutions, dried ($MgSO_4$) and evaporated. The residue was distilled in vacuo to give title compound (59.66 g, 78%) as a colorless liquid, bp 115°-118° C. (1 mmHg).

TLC ($CH_2Cl_2$-hexane; 4:1) $R_f$=0.30.

B.
3-(4'-Fluorophenyl)-3-oxo-2-(2-pyridinylmethylene)-propanoic acid, ethyl ester To a mixture of Part A compound (15.75 g, 75 mmole) and pyridine-2-carboxaldehyde (8.03 g, 75 mmol) at room temperature under argon was added piperidine (3 drops). After stirring at room temperature for 16 hours and at 80° C. (bath temperature) for 4 hours, the mixture crystallized. The cooled mixture was triturated with $Et_2O$, the crystalline product collected by suction and washed with $Et_2O$ until the washings were colorless to give crude title compound (19.68 g, 88%) as a gray solid. The crude product was recrystalized from EtOAc-hexane (charcoal) to give pure title compound (18.98 g, 85%) as pale yellow crystals, mp 128°-129° C.

TLC ($Et_2O$-hexane; 3:7) $R_f$=0.21 ($R_f$of Part A compound=0.30).

C.
2-(4'-Fluorobenzoyl)-3-(1-methylethyl)-3-(2-pyridine)-propanoic acid, ethyl ester To a solution of 2.0 M isopropylmagnesium chloride (19.0 mL, 38.0 mmol) in dry THF (200 mL) at 0° C. under argon was added cuprous iodide (0.40 g, 2.1 mmol). After stirring at 0° C. for 2-5 minutes, the mixture was cooled to −78° C. (bath temperature) and treted dropwise over 5 minutes with a solution of Part B compound (10.45 g, 34.9 mmole) in dry THF (75 mL). The resulting solution was allowed to warm to −50° C., maintained at −50 to −55° C. for 1 hour, treated with an additional portion of cuprous iodide (0.40 g) and allowed to warm to room temperature. After stirring at room temperature for 3 hours, the reaction was quenched with saturated $NH_4Cl$ solution (100 mL). The organic phase was separated, washed with saturated $NH_4Cl$, saturated $NaHCO_3$ and saturated NaCl solutions, dried ($Na_2SO_4$) and evaporated to dryness. The crude product was purified by flash chromatography on silica gel eluting with EtOAc-hexane (15:85) to give title compound (9.765 g, 81.5%) as a green, viscous oil.

TLC (EtOAc-hexane; 1:1) $R_f$=0.44 and 0.38 (mixture of isomers; $R_f$of Part B compound=0.30).

D.
3-(4-Fluorophenyl)-1-(1-methylethyl)-2-indolizinecarboxylic acid, ethyl ester A solution of Part C compound (9.765 g, 28.5 mmole) in acetic anhydride (120 mL) was refluxed under argon for 2.5 hours. The resulting black solution was evaported to dryness. The residue was purified by flash chromatography on silica gel eluting with $Et_2O$-hexane (3:100) to give title compound (3.820 g, 41%) as a pale yellow oil which crystallized on standing, mp 51°-52° C.

TLC (EtOAc-hexane; 3:7) $R_f$=0.58.

E.
3-(4-Fluorophenyl)-1-(1-methylethyl)-2-indolizinemethanol

To a suspension of $LiAlH_4$ (0.90 g, 23.7 mmol) in dry THF (40 mL) at 0° C. under argon was added dropwise a solution of Part D compound (2.10 g, 6.46 mmol) in THF (15 mL). After stirring at 0° C. for 30 minutes and at room temperature for 3 hours, the mixture was again placed in an ice bath and treated succesively with H$_2$O (0.9 mL), 15% NaOH (0.9 mL) and H$_2$O (2.7 mL), then allowed to warm to room temperature. The resulting suspension was filtered through Celite and evaported to dryness to give crude title compound (1.796 g) as a yellow foam. The crude product was crystallized from Et$_2$O-hexanes to give pure title compound (1.708 g, 93%) as yellow crystals, mp 94°-95° C.

TLC (EtOAc-hexane; 3:7) R$_f$=0.47.

Anal. Calc'd for C$_{18}$H$_{18}$NOF: C, 76.30; H, 6.40; N, 4.94; F, 6.71. Found: C, 76.14; H, 6.35; N, 4.91; F, 6.47.

F.

3-(4-Fluorophenyl)-1-(1-methylethyl)-2-indolizinecarboxaldehyde

To a solution of Part E compound (1.567 g, 5.54 mmol) in dry THF (35 mL) at 0° C. under argon was added dropwise via syringe 3.0 M methylmagnesium bromide-Et$_2$O (1.90 mL, 5.70 mmol). When the addition was complete the mixture was allowed to warm to room temperature. After stirring at room temperature for 30 minutes, the mixture was treated dropwise with a solution of 1,1'-(azodicarbonyl)dipiperidine (1.550 g, 6.15 mmol) in dry THF (10 mL). After stirring at room temperature for 3 hours, the reaction was quenched with saturated NaCl solution (30 mL). The organic phase was separated, washed with saturated NaHCO$_3$ and saturated NaCl solutions, dried (Na$_2$SO$_4$) and evaporated to dryness. The residue was taken up in Et$_2$O-hexane (1:1, 100 mL), filtered and the filtrate evaportated to a yellow foam. The crude product was purified by flash chromatography on silica gel eluting with Et$_2$O-hexane (3:100) to give title compound (1.449 g, 93%) as a yellow foam. The crude product was crystallized from hexane to give pure title compound (1.411 g, 91%) as yellow crystals, mp 97°-98° C.

TLC (EtOAc-hexane; 3:7) R$_f$=0.60.

Anal. Calc'd for C$_{18}$H$_{16}$NOF: C, 76.85; H, 5.73; N, 4.98; F, 6.75. Found: C, 76.69; H, 5.73; N, 5.02; F, 6.62.

G.

2-(2,2-Dibromoethenyl)-3-(4-fluorophenyl)-1-(1-methylethyl)indolizine

To a solution of Part F compound (1.351 g, 4.81 mmol) and triphenylphosphine (5.04 g, 19.2 mmol) in dry CH$_2$Cl$_2$ (20 mL) at −30 to −25° C. (bath temperature) under argon was added dropwise over 30 minutes a solution of carbon tetrabromide (3.19 g, 9.62 mmol) in CH$_2$Cl$_2$ (15 mL). After stirring at −25° C. for an additional 1 hour, the dark green mixture was treated with saturated NaHCO$_3$ solution (25 mL) and allowed to warm to room temperature. The organic phase was separated, dried (Na$_2$SO$_4$) and evaporated to dryness. The crude product was purified by flash chromatography on silica gel eluting with CH$_2$Cl$_2$-hexane (5:95) to give title compound (1.672 g, 80%) as a yellow foam. The crude product was crystallized from hexane to give pure title product (1.590 g, 76%) as pale yellow crystals, mp 118.5°-119.5° C.

TLC (EtOAc-hexane; 1:4) R$_f$=0.66.

Anal. Calc'd for C$_{19}$H$_{16}$NBr$_2$F: C, 52.20; H, 3.69; N, 3.21; Br, 36.50; F, 4.34. Found: C, 52.12; H, 3.71; N, 3.20; Br, 36.60; F, 4.39.

H.

(s)-3-[[(1,1-Dimethylethyl)diphenylsilyl]oxy]-4-[[[3-(4-fluorophenyl)-1-(1-methylethyl)-2-indolizinyl]ethynyl]-methoxyphosphinyl]butanoic acid, methyl ester To a solution of 1.6 M n-C$_4$H$_9$Li-hexane (3.85 mL, 6.16 mL) in dry THF (10 mL) at −78° C. under argon was added dropwise a solution of Part G compound (1.310 g, 3.00 mmol) in THF (15 mL) over 15 minutes. After stirring at −78° C. for 1.5 hours, the anion solution was transferred via cannula to a −78° C. solution of Example 1, Part H compound (ca. 4.80 mmol) in dry THF (15 mL). After stirring at −78° C. for 1.5 hours, the reaction was quenched by the dropwise addition of saturated NH$_4$Cl (20 mL) and allowed to warm to room temperature. The mixture was extracted with EtOAc, the extracts washed with 5% KHSO$_4$, saturated NaHCO$_3$ and saturated NaCl solutions, dried (Na$_2$SO$_4$) and evaporated to dryness. The crude product was purified by flash chromatography on silica gel eluting with EtOAc-hexane (3:7) to give title compound (1.861 g, 80% based on Part G compound) as a yellow foam.

TLC (acetone-hexane; 1:1) R$_f$=0.56.

I.

(S)-4-[[[3-(4-Fluorophenyl)-1-(1-methylethyl)-2-indolizinyl]ethynyl]methoxyphssphinyl]-3-hydroxybutanoic acid, methyl ester To a solution of Part H compound (1.851 g, 2.61 mmol) in dry THF (10 mL) at room temperature under argon was added glacial acetic acid (0.59 mL, 10.3 mmol) and a 1.0 M solution of (n-C$_4$H$_9$)$_4$NF in THF (7.70 mL, 7.70 mmol). After stirring at room temperature for 40 hours, the mixture was diluted with EtOAc (50 mL), washed successively with 1N HCl (3×50 mL) and saturated NaCl solutions, dried (Na$_2$SO$_4$) and evaporated to dryness. The residue was taken up in CH$_2$Cl$_2$ (8 mL)-Et$_2$O (30 mL), cooled in an ice bath and treated with excess etheral diazomethane. The residue obtained by evaporation of the ether was purified by flash chromatography on silica gel eluting with acetone-hexane (3:7) to give title ester (1.076 g, 87.5%) as a yellow glass.

TLC (acetone-hexane; 1:1) R$_f$=0.23.

EXAMPLE 4

(S)-4-[[[3-(4-Fluorophenyl)-1-(1-methylethyl)-2-indolizinyl]ethynyl]hydroxyphosphinyl]-3-hydroxybutanoic acid, dilithium salt To a solution of Example 3 compound (1.076 g, 2.28 mmol) in dioxane (8 mL) at room temperature under argon was added 1N LiOH solution (6.8 mL, 6.8 mmol). After stirring at room temperature for 3 hours, the mixture was evaporated to dryness. The crude product was suspended in water and applied to a sort pad of CHP-20 (30 mL bed volume, 1 inch diameter), eluted with water (200 mL) followed by CH$_3$OH-water (25:75; 200 mL) and CH$_3$OH-water (50:50; 200 mL). The product containing fractions were combined and evaportated to dryness. The solid residue was triturated with water-acetonitrile to give pure title compound (1.056 g, 91%) as a pale yellow solid, mp 290°-294° C. (d).

[α]$_D$=+5.2° (c=0.60, CH$_3$OH); [α]$_{436}$=+16.3° (c=0.60, CH$_3$OH).

TLC (i-C$_3$H$_7$OH-concentrated NH$_4$OH-H$_2$O; 7:2:1) R$_f$=0.44.

Anal. Calc'd for 3.0 mole H₂O: C, 54 24; H, 5.34; N, 2.75; F, 3.73; P, 6.08. Found: C, 54.38; H, 5.37; N, 2.86; F, 3.72; P, 6.18.

EXAMPLE 5

(S)-4-[[[1-(4-Fluorophenyl)-5,6,7,8-tetrahydro-3-(1-methylethyl)indolizin-2-yl]ethynyl]methoxyphosphinyl]-3-hydroxybutanoic acid, methyl ester

A.

1-(4-Fluorophenyl)-5,6,7,8-tetrahydro-3-(1-methylethyl)-2-indolizinecarboxylic acid, ethyl ester To a solution of Example 1, Part C compound 6.50 g, 20.0 mmol) in EtOAc (35 mL)-CH₃OH (70 mL) was added 10% Pd-C (1.5 g) and the resulting mixture hydrogenated in a Parr apparatus at 50 psi for 20 hours. The catalyst was removed by filtration through Celite and the filtrate evaporated to a colorless, viscous oil. The crude product was crystallized from hexane to give pure title compound (6.292 g, 96%) as white crystals, mp 85.5°-86.5° C.

TLC (EtOAc-hexane; 3:7) Rf=0.38 (Rf of Example 1, Part C compound, 0.43).

Anal. Calc'd for C₂₀H₂₄NO₂F C, 72.92; H, 7.34; N, 4.25; F, 5.77. Found: C, 72.75; H, 7.40; N, 4.28; F, 5.73.

B.

1-(4-Fluorophenyl)-5,6,7,8-tetrahydro-3-(1-methylethyl)-2-indolizinemethanol

To a suspension of LiAlH₄ (2 30 g. 60.5 mmol) in dry THF (100 mL) at 0° C. under argon was added dropwise a solution of Part A compound (6.00 g, 18.2 mmol) in THF (20 mL). After stirring at 0° C. for 15 minutes, at room temperature for 2 hours and at 60°-65° C. (bath temperature) for 2 hours, the mixture was again placed in an ice bath and treated succesively with H₂O (2.3 mL), 15% NaOH (2.3 mL) and H₂O (6.9 mL), then allowed to warm to room temperature. The resulting suspension was filtered through Celite and evaporated to dryness to give crude title compound (5.492 g) as a white solid. The crude product was crystallized from hexanes to give pure title compound (5.274 g, 100%) as white crystals, mp 97°-99° C.

TLC (EtOAc-hexane; 3:7) R$_f$=0.46.

C.

1-(4-Fluorophenyl)-5,6,7,8-tetrahydro-3-(1-methylethyl-2-indolizinecarboxaldehyde To a solution of Part B compound (4.783 g, 16.66 mmol) in dry THF (90 mL) at 0° C. under argon was added dropwise via syringe 3.0 M methylmagnesium bromide-Et₂O (5.60 mL, 16.8 mmol). When the addition was complete the mixture was allowed to warm to room temperature. After stirring at room temperature for 30 minutes, the resulting mixture was treated dropwise with a solution of 1,1'-(azodicarbonyl)dipiperidine (4.410 g, 17.5 mmol) in dry THF (35 mL). After stirring at room temperature for 2.5 hours, the reaction was quenched with saturated NaCl solution (50 mL). The organic phase was separated, washed with saturated NaHCO₃ and saturated NaCl solutions, dried (Na₂SO₄) and evaporated to dryness. The residue was taken up in Et₂O-hexane (1:1, 100 mL), filtered and the filtrate evaporated to a colorless foam. The crude product was purified by flash chromatography on silica gel eluting with Et₂O-hexane (1:9) to give pure title compound (3.709 g, 78%) as a white crystalline solid after crystallization from cold hexane, mp 145°-146° C.

TLC (EtOAc-hexane; 3:7) R$_f$=0.46.

D.

1-(4-Fluorophenyl)-5,6,7,8-tetrahydro-3-(1-methylethyl)-o-(trichloromethyl)-2-indolizinemethanol, acetate ester To a solution of Part C compound (1.292 g, 4.53 mmol) and chloroform (1.80 mL, 22.5 mmol) in dry THF (20 mL) at −78° C. (bath temperature) under argon was added dropwise via syringe over 35 minutes (syringe pump) a solution of 1.0M lithium bis(trimethylsilyl)amide-THF (5.0 mL, 5.0 mmol). After stirring at −78° C. for an additional 45 minutes, the reaction was quenched by the addition of saturated NH₄Cl solution (10 mL) and allowed to warm to room temperature. The mixture was extracted with EtOAc (50 mL), the extract washed with water, 5% KHSO₄, saturated NaCl solutions, dried (Na₂SO₄) and evaporated to dryness. The crude product was immediately taken up in acetic anhydride (6 mL)-pyridine (4 mL). After stirring at 60°-65° C. (bath temperature) for 4 hours and at room temperature for 16 hours, the mixture was evaporated to dryness. The crude product was purified by flash chromatography on silica gel eluting with Et₂O-hexane (5:100) to give title compound (1.719 g, 85%) as a pale yellow, viscous oil. The crude product was crystallized from Et₂O-hexane to give pure title compound (1.685 g, 83%) as white crystals, mp 150°-152° C. (d).

TLC (EtOAc-hexane; 3:7) R$_f$=0.60 (F$_f$ of Part C compound, 0.44; R$_f$ of intermediate trichlorocarbinol, 0.55).

E.

2-(2,2-Dichloroethenyl)-1-(4-fluorophenyl)-5,6,7,8-tetrahydro-3-(1-methylethyl)indolizine To a solution of Part D compound (1.657 g, 3.71 mmol) in dry DMF (15 mL) at room temperature under argon was added PbCl₂ (0.103 g, 0.37 mmol) and aluminum foil (0.120 g, 4.45 mmol) cut into small pieces. After stirring at room temperature for 20 minutes, an exothermic reaction occurred. After stirring for an additional 4 hours, the solution was decanted from the unreacted aluminum foil and partitioned between EtOAc/5% KHSO₄. The organic phase was washed with water, 5% KHSO₄ and saturated NaCl solutions, dried (Na₂SO₄) and evaporated to dryness. The crude product was purified by flash chromatography on silica gel eluting with CH₂Cl₂-hexane (5:95) to give title compound (1.137 g, 87%) as a white solid. Trituration with hexane gave pure title compound (1.105 g, 85%) as white crystals, mp 118°-120° C.

TLC (EtOAc-hexane; 1:4) R$_f$=0.55.

F.

(S)-3-[[(1,1-Dimethylethyl)diphenylsilyl]oxy]-4-[[[1-(4-fluorophenyl)-5,6,7,8-tetrahydro-3-(1-methylethyl)-2-indolizinyl]ethynyl]methoxyphosphinyl]butanoic acid, methyl ester To a solution of 1.6M n-butyllithium-hexane (3.65 mL, 5.84 mol) in dry THF (15 mL) at −78° C. under argon was added dropwise a solution of Part E compound (1.003 g, 2.85 mmol) in THF (10 mL) over 15 minutes After stirring at −78° C. for 1 hour, the anion solution was transferred via cannula to a −78° C. solution of Example 1, Part H compound (ca. 4.80 mmol) in dry THF (15 mL). After stirring at -78° C. for 1 hour, the reaction was quenched by the dropwise addition of saturated NH₄Cl (10 mL) and allowed to warm to room temperature. The mixture was extracted with EtOAc (100 mL), the extract washed with water, 5% KHSO$_4$, saturated NaHCO$_3$ and saturated NaCl solutions, dried (Na$_2$SO$_4$) and evaporated to dryness. The crude product was purified by flash chromatography on silica gel eluting with EtOAc-hexane (1:1) to give title compound (1.801 g, 89% based on Part E compound) as a pale yellow foam.

TLC (acetone-hexane; 1:1) R$_f$=0.38.

G.
(S)-4-[[[1-(4-Fluorophenyl)-5,6,7,8-tetrahydro-3-(1-methylethyl)indolizin-2-yl]ethynyl]methoxyphosphinyl]-3-hydroxybutanoic acid, methyl ester To a solution of Part F compound (1.790 g, 2.51 mmol) in dry THF (10 mL) at room temperature under argon was added glacial acetic acid (AcOH) (0.59 mL, 10.3 mmol) and a 1.0 M solution of (n-C$_4$H$_9$)$_4$NF in THF (7.70 mL, 7.70 mmol). After stirring at room temperature for 36 hours, the mixture was diluted with EtOAc (100 mL), washed successively with 1N HCl (4×50 mL) and saturated NaCl solutions, dried (Na$_2$SO$_4$) and evaporated to dryness. The residue was taken up in CH$_2$Cl$_2$ (8 mL)-Et$_2$O (30 mL), cooled in an ice bath and treated with excess etheral diazomethane. The residue obtained by evaporation of the ether was purified by flash chromatography on silica gel eluting with acetone-hexane (2:3) to give title ester (1.043 g, 87%) as a colorless glass.

TLC (acetone-hexane; 1:1) R$_f$=0.26.

EXAMPLE 6
(S)-4-[[[1-(4-Fluorophenyl)-5,6,7,8-tetrahydro-3-(1-methylethyl)indolizin-2-yl]ethynyl]hydroxyphosphinyl]-3-hydroxybutanoic acid, disodium salt To a solution of Example 5 compound (0.617 g, 1.30 mmol) in dioxane (6 mL) at room temperature under argon was added 1N NaOH solution (4.0 mL, 4.0 mmol). After stirring at room temperature for 3 hours, the mixture was evaporated to dryness. The crude product was purified on CHP-20 (20 mL bed volume, 1 inch diameter) eluting with water (300 mL) followed by MeOH-water (3:7; 300 mL). The product containing fractions were combined and evaporated to dryness. The residue was taken up in water (2 mL) and diluted with acetonitrile (20 mL). The solution was decanted from the gummy precipitate and discarded. The residue was taken up in water, filtered and lyophilized to give pure title compound (0.621 g, 94° %) as a fluffy, white solid.

[α]$_D$=+4.9° (c=0.51, CH$_3$OH); [α]$_{365}$=+19.6° (c=0.51, CH$_3$OH).

TLC (i-C$_3$H$_7$OH-conc. NH$_4$OH-H$_2$O; 7:2:1) R$_f$=0.46.

Anal. Calc'd for 1.03 mole H$_2$O C, 54.16; H, 5.35; N, 2.75; F, 3.73; P, 6.07. Found: C, 54.14; H, 5.52; N, 2.77; F, 3.81; P, 6.40.

EXAMPLE 7
(S)-4-[[2-[1-(4-Fluorophenyl)-5,6,7,8-tetrahydro-3-(1-methylethyl)-2-indolizinyl]ethyl]methoxyphosphinyl]-3-hydroxybutanoic acid, methyl ester To a solution of Example 6 compound (0.414 g, 0.872 mmol) in MeOH (40 mL) was added 10% Pd-C (0.16 g) and the resulting mixture hydrogenated in a Parr apparatus at 35 psi for 4.5 hours. The catalyst was removed by filtration through Celite and the filtrate evaporated to give crude title ester (0.422 g, 100%) as a colorless foam.

TLC (acetone-hexane; 1:1) R$_f$=0.35 (Rf of Example 6 compound, 0.42).

EXAMPLE 8
(S)-4-[[2-[1-(4-Fluorophenyl)-5,6,7,8-tetrahydro-3-(1-methylethyl)-2-indolizinyl]ethyl]hydroxyphosphinyl]-3-hydroxybutanoic acid, dilithium salt To a solution of Example 7 compound (0.422 g, ca. 0.872 mmol) in dioxane (5 mL) at room temperature under argon was added 1N LiOH solution (2.6 mL, 2.6 mmol). After stirring at room temperature for 1 hour and at 60°-65° C. (bath temperature) for 2 hours, the mixture was evaported to dryness. The crude product was suspended in water (5 mL) and purified over CHP-20 (20 mL bed volume, 1 inch diameter) eluting with water (200 mL) followed by MeOH-water (1:1; 200 mL). The product containing fractions were combined and evaporated to dryness. The residue was triturated with acetonitrile-water to give pure title compound (0.357 g, 83%) as a white solid, mp 300°-310° C. (d).

[α]$_D$=−3.9° (c=0.54, CH$_3$OH); [α]$_{436}$=−9.5° (c=0.54, CH$_3$OH).

TLC (i-C$_3$H$_7$OH-concentrated NH$_4$OH-H$_2$O; 7:2:1) R$_f$=0.58.

Anal. Calc'd for 1.5 mole H$_2$O: C, 56.31; H, 6.58; N, 2.86; F, 3.87; P, 6.31. Found: C, 56.37; H, 6.63; N, 2.80; F, 4.04; P, 6.59.

EXAMPLE 9
(S)-4-[[[3-(4-Fluorophenyl)-5,6,7,8-tetrahydro-1-(1-methylethyl)-2-indolizinyl]ethynyl]methoxyphosphinyl]-3-hydroxybutanoic acid, methyl ester

A.
3-(4-Fluorophenyl)-5,6,7,8-tetrahydro-1-(1-methylethyl)-2-indolizinecarboxylic acid, ethyl ester To a solution of Example 3, Part D compound (2.193 g, 6.75 mmol) in CH$_3$OH (50 mL) was added 10% Pd-C (0.52 g) and the resulting mixture hydrogenated in a Parr apparatus at 50 psi for 7 hours. The catalyst was removed by filtration through Celite and the filtrate evaporated to give crude title compound (2.116, 95%) as a colorless, viscous oil. The crude product was crystallized from CH$_3$OH-water to give pure title compound (2.097 g, 94%) as white crystals, mp 76°-78° C.

TLC (EtOAc-hexane; 3:7) R$_f$=0.51 (R$_f$of Example 3, Part D compound, 0.57).

B.
3-(4-Fluorophenyl)-5,6,7,8-tetrahydro-1-(1-methylethyl)-2-indolizinemethanol To a suspension of LiAlH$_4$ (0.790 g, 20.8 mmol) in dry THF (25 mL) at 0° C. under argon was added dropwise a solution of Part A compound (2.050 g, 6.23 mmol) in THF (10 mL). After stirring at 0° C. for 15 minutes, at room temperature for 1 hour and at 60-65° C. (bath temperature) for 2 hours, the mixture was again placed in an ice bath and treated succesively with H$_2$O (0.8 mL), 15% NaOH (0.8 mL) and H$_2$O (2.4 mL), then allowed to warm to room temperature. The resulting suspension was filtered through Celite and evaported to dryness. The crude product was purified by flash chromatography on silica gel eluting with Et$_2$O-hexane (15:85) to give title compound (1.777 g, 99%) as a colorless oil. The crude product was crystallized from hexanes to give pure title compound (1.532 g, 86%) as white crystals, mp 75°–78° C.

TLC (EtOAc-hexane; 3:7) $R_f$=0.50.

C.
3-(4-Fluorophenyl)-5,6,7,8-tetrahydro-1-(1-methylethyl)-2-indolizinecarboxaldehyde To a solution of Part B compound (1.727 g, 6.02 mmol) in dry THF (35 mL) at 0° C. under argon was added dropwise via syringe 3.0 M methylmagnesium bromide-Et$_2$O (2.02 mL, 6.06 mmol). When the addition was complete the mixture was allowed to warm to room temperature. After stirring at room temperature for 30 minutes, the resulting mixture was treated dropwise with a solution of 1,1'-(azodicarbonyl)dipiperidine (1.595 g, 6.33 mmol) in dry THF (35 mL). After stirring at room temperature for 2 hours, the reaction was quenched with saturated NaCl solutin (50 mL). The organic phase was separated, diluted with EtOAc (50 mL), washed with saturated NaHCO$_3$ and saturated NaCl solutions, dried (Na$_2$SO$_4$) and evaporated to dryness. The residue was taken up in Et$_2$O-hexane (1:1, 100 mL), filtered and the filtrate evaporated to a colorless foam. The crude product was purified by flash chromatography on silica gel eluting with Et$_2$O-hexane (1:9) to give pure title compound (1.519 g, 89%) as a colorless oil. The purified product was crystallized from hexanes to give pure title compound (1.450 g, 84.5%) as white crystals, mp 100° -101° C.

TLC (EtOAc-hexane; 3:7) $R_f$=0.64.

D.
3-(4-Fluorophenyl)-5,6,7,8-tetrahydro-1-(1-methylethyl)-α-(trichloromethyl)-2-indolizinemethanol, acetate ester To a solution of Part C compound (1.356 g, 4.76 mmol) and chloroform (1.90 mL, 23.7 mmol) in dry THF (20 mL) at −78° C. (bath temperature) under argon was added dropwise via syringe over 40 minutes (syringe pump) a solution of 1.0M lithium bis(trimethylsilyl)amide-THF (5.25 mL, 5.25 mmol). After stirring at −78° C. for an additional 40 minutes, the reaction was quenched by the addition of saturated NH$_4$Cl solution (10 mL) and allowed to warm to room temperature. The mixture was extracted with EtOAc (50 mL), the extract washed with water, 5% KHSO$_4$, saturated NaHCO$_3$ and saturated NaCl solutions, dried (Na$_2$SO$_4$) and evaporated to dryness. The crude product was immediately taken up in acetic anhydride (6 mL)-pyridine (4 mL). After stirring at 60°–65° C. (bath temperature) for 3 hours and at room temperature for 16 hours, the mixture was evaporated to dryness. The crude product was purified by flash chromatography on silica gel eluting with Et$_2$O-hexane (5:100) to give title compound (1.934 g, 91%) as a colorless foam. The crude product was crystallized from hexane to give pure title compound (1.809 g, 85%) as white crystals, mp 153°–154° C.

TLC (EtOAc-hexane; 3:7) $R_f$=0.60 ($R_f$ of Part C compound, 0.49; $R_f$ of intermediate trichlorocarbinol, 0.56).

E.
2-(2,2-Dichloroethenyl)-3-(4-fluorophenyl)-5,6,7,8-tetrahydro-1-(1-methylethyl)indolizine To a solution of Part D compound (1.767 g, 3.96 mmol) in dry DMF (15 mL) at room temperature under argon was added PbCl$_2$ (0.110 g, 0.396 mmol) and aluminum foil (0.128 g, 4.74 mmol) cut into small pieces. After stirring at room temperature for 20 minutes, an exothermic reaction occurred. After stirring for an additional 3 hours, the solution was decanted from the unreacted aluminum foil and partitioned between EtOAc-5% KHSO$_4$. The organic phase was washed with water, 5% KHSO$_4$ and saturated NaCl solutions, dried (Na$_2$SO$_4$) and evaporated to dryness. The crude product was purified by flash chromatography on silica gel eluting with CH$_2$Cl$_2$-hexane (5:95) to give title compound (1.258 g, 90%) as a colorless glass. The purified product was crystallized from CH$_3$CN-water to give pure title compound (1.189 g, 85%) as white crystals, mp 97°–98° C.

TLC (EtOAc-hexane; 1:4) $R_f$=0.64.

F.
(S)-4-(Chloromethoxyphosphinyl)-3-[[(1,1-dimethylethyl)diphenylsilyl]oxy]butanoic acid, methyl ester The dicyclohexylamine salt of Example 1, Part G (3.420 g, 5.40 mmol) was partitioned between EtOAc-5% KHSO$_4$ (100 mL each). The organic phase was washed with 5% KHSO$_4$ (4×50 mL) and saturated NaCl solutions, dried (Na$_2$SO$_4$) and evaporated to a colorless viscous oil. The free acid was taken up in dry CH$_2$Cl$_2$ (15 mL) and treated with trimethylsilyldiethylamine (2.08 mL, 11.0 mmole). After stirring at room temperature under argon for 1.5 hours, the mixture was evaporated to dryness, taken up in dry benzene (10 mL) and again evaporated to dryness. The crude silyl ester was taken up in CH$_2$Cl$_2$ (15 mL) placed in an ice bath under argon and treated with oxalyl chloride (0.50 mL, 5.73 mmole) and DMF (85 µL, 1.1 mmol). After stirring at 0° C. for 15 minutes and at room temperature for 1 hour, the mixture was evaporated to dryness. The residue was taken up in benzene (15 mL), filtered through sinctered glass and evaporated to dryness to give crude title compound (ca. 5.40 mmol) as a pale yellow, viscous oil.

G.
(s)-3-[[(1,1-Dimethylethyl)diphenylsilyl]oxy]-4-[[[3-(4-fluorophenyl)-5,6,7,8-tetrahydro-1-(1-methylethyl)-2-indolizinyl]ethynyl]methoxyphosphinyl]butanoic acid, methyl ester To a solution of 1.6M n-C$_4$H$_9$Li-hexane (4.15 mL, 6.64 mol) in dry THF (15 mL) at −78° C. under argon was added dropwise a solution of Part E compound (1.142 g, 3.24 mmol) in THF (10 mL) over 15 minutes After stirring at −78° C. for 1.5 hours, the anion solution was transferred via cannula to a −78° C. solution of Part F compound (ca. 5.40 mmol) in dry THF (20 mL). After stirring at −78° C. for 45 minutes, the reaction was quenched by the dropwise addition of saturated NH4Cl (10 mL) and allowed to warm to room temperature. The mixture was extracted with EtOAc (100 mL), the extract washed with water, 5% KHSO$_4$, saturated NaHCO$_3$ and saturated NaCl solutions, dried (Na$_2$SO$_4$) and evaporated to dryness. The crude product was purified by flash chromatography on silica gel eluting with EtOAc-toluene (15:85) to give title compound (1.873 g, 81% based on Part D compound) as a pale yellow glass.

TLC (acetone-hexane; 1:1) $R_f$=0.56.

H.

(S)-4-[[[3-(4-Fluorophenyl)-5,6,7,8-tetrahydro-1-(1-methylethyl)-2-indolizinyl]ethynyl]methoxyphosphinyl]-3-hydroxybutanoic acid, methyl ester To a solution of Part G compound (1.859 g, 2.61 mmol) in dry THF (6 mL) at room-temperature under argon was added glacial acetic acid (0.61 mL, 10.7 mmol) and at 1.0M solution of (n-C$_4$H$_9$)$_4$NF in THF (8.0 mL, 8.0 mmol). After stirring at room temperature for 40 hours, the mixture was diluted with EtOAc (100 mL), washed successively with 1N HCl (4×50 mL) and saturated NaCl solutions, dried (Na$_2$SO$_4$) and evaporated to dryness. The residue was taken up in CH$_2$Cl$_2$ (8 mL)-Et$_2$O (30 mL), cooled in an ice bath and treated with excess etheral diazomethane. The residue obtained by evaporation of the ether was purified by flash chromatography on silica gel eluting with acetonehexane (3:7) to give title ester (1.076 g, 85%) as a colorless glass.

TLC (acetone-hexane; 1:1) R$_f$=0.28.

EXAMPLE 10

(S)-4-[[[3-(4-Fluorophenyl)-5,6,7,8-tetrahydro-1-(1-methylethyl)-2-indolizinyl]ethynyl]hydroxyphosohinyl]-3-hydroxybutanoic acid, dilithium salt To a solution of Example 9 compound (0.633 g, 1.33 mmol) in dioxane (6 mL) at room temperature under argon was added 1N LiOH solution (4.0 mL, 4.0 mmol). After stirring at room temperature for 2 hours, the mixture was evaporated to dryness. The crude product was purified on CHP-20 (20 mL bed volume, 1 inch diameter) eluting with water (300 mL) followed by CH$_3$OH-water (3:7; 300 mL). The product containing fractions were combined and evaporated to dryness. The residue was triturated with acetonitrile to give pure title compound (0.578 g, 89%) as a white solid, mp 265° C. (d).

[α]$_D$=+3.0° (c=0.59, CH$_3$OH); [α]$_{436}$+6.4° (c=0.59, CH$_3$OH).

TLC (i-C$_3$H$_7$OH-concentrated NH$_4$OH-H$_2$O; 7:2:1) R$_f$=0.45.

Anal. Calc'd for 1.5 mole H$_2$O: C, 56.81; H, 5.80; N, 2.88; F, 3.91; P, 6.37. Found: C, 56.99; H, 5.70; N, 2.86; F, 3.88; P, 5.99.

EXAMPLE 11

(S)-4-[[2-[3-(4-Fluorophenyl)-5,6,7,S-tetrahydro-1-(1-methylethyl)-2-indolizinyl]ethyl]methoxyphosphinyl]-3-hydroxybutanoic acid, methyl ester To a solution of Example 9 compound (0.413 g, 0.869 mmol) in CH$_3$OH (40 mL) was added 10% Pd-C (0.16 g) and the resulting mixture hydrogenated in a Parr apparatus at 50 psi for 4 hours. The catalyst was removed by filtration through Celite and the filtrate evaporated to dryness. The crude product was purified by flash chromatography on silica gel eluting with isopropanol-hexane (1:9) to give title ester (0.359 g, 86%) as a colorless foam.

TLC (acetone-hexane: 1:1) R$_f$=0.32 (R$_f$ of Example 9 compound, 0.37).

EXAMPLE 12

(S)-4-[[2-[3-(4-Fluorophenyl)-5,6,7,8-tetrahydro-1-(1-methylethyl)-2-indolizinyl]ethyl]hydroxyphosphinyl]-3-hydroxybutanoic acid, dilithium salt To a solution of Example 11 compound (0.359 g, 0.749 mmol) in dioxane (5 mL) at room temperature under argon was added 1N LiOH solution (2.7 mL, 2.7 mmol). After stirring at 60°-65° C. (bath temperature) for 1 hour, the mixture was evaporated to dryness. The crude product was purified over CHP-20 (20 mL bed volume, 1 inch diameter) eluting with water (200 mL) followed by CH$_3$OH-water (3:7; 200 mL). The product containing fractions were combined and evaporated to dryness. The residue was triturated with acetonitrile-water and then with Et$_2$O to give pure title compound (0.304 g, 83%) as a white solid, mp 310°-330° C. (d).

[α]$_D$=−6.5° (c=0.54, CH$_3$OH); [α]$_{436}$=−13.2° (c=0.54, CH$_3$OH).

TLC (i-C$_3$H$_7$OH-concentrated NH$_3$OH-H$_2$O; 7:2:1) R$_f$=0.49.

Anal. Calc'd for 1.5 mole H$_2$O: C, 56.31; H, 6.58; N, 2.86; F, 3.87; P, 6.31. Found: C, 56.24; H, 6.34; N, 2.57; F, 3.91; P, 6.11.

Following the procedure described in the heretofore described working Examples, the following additional compounds of the invention may be prepared.

$$R-\overset{O}{\underset{\underset{Z}{\overset{|}{X}}}{\overset{\|}{P}}}-CH_2-\overset{\overset{H}{|}}{\underset{\underset{OH}{}}{C}}-CH_2-CO_2-R^x$$

| Example No. | R | Z | X | R$^x$ |
|---|---|---|---|---|
| 13 | OH | 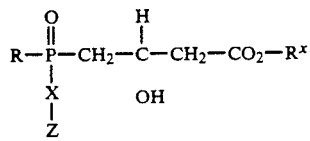 | —CH$_2$CH$_2$— | H |

-continued

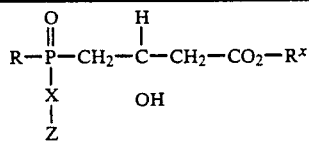

| Example No. | R | Z | X | $R^x$ |
|---|---|---|---|---|
| 14 | $C_2H_5O$ | (3-methyl-2-(4-fluorophenyl)indolizine) | —CH=CH— | $CH_3$ |
| 15 | OH | (n-$C_3H_7$, 3-methyl-2-(3-trifluoromethylphenyl), fused cyclohexane-pyridine) | —C≡C— | H |
| 16 | OLi | ($CH_3$-phenyl, 3-methyl, $C_5H_{11}$, fused cyclohexane-pyridine) | —CH=CH— | Li |
| 17 | OH | (i-$C_3H_7$, 3-methyl-2-(3-fluorophenyl)indolizine) | —C≡C— | H |

What is claimed is:

1. A compound having the structure

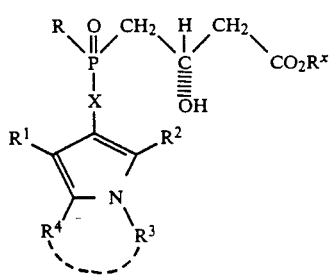

wherein X is —$(CH_2)_a$—, —CH=CH—, or —C≡C—; a is 1,2 or 3; R is OH or lower alkoxy; $R^x$ is alkali metal, lower alkyl or H; one of $R^1$ and $R^2$ is substituted phenyl and the other of $R^1$ and $R^2$ is lower alkyl; $R^3$ and $R^4$ together are —CH=CH—$_2$ or —$CH_2$—$_4$ and are joined to complete a six-membered carbocyclic ring.

2. The compound as defined in claim 1 having the structure

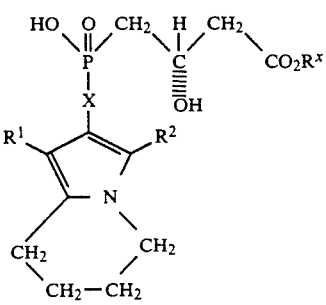

3. The compound as defined in claim 1 having the structure

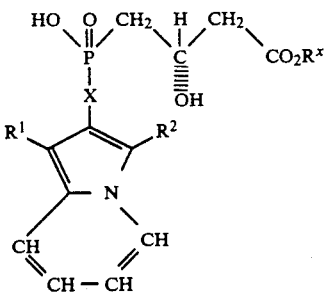

4. The compound as defined in claim 1 wherein X is —CH₂CH₂—.

5. The compound as defined in claim 1 wherein X is —CH=CH(E)—.

6. The compound as defined in claim 1 wherein X is —C≡C—.

7. The compound as defined in claim 1 wherein R is OH.

8. The compound as defined in claim 1 wherein R¹ is lower alkyl and R² is substituted phenyl.

9. The compound as defined in claim 1 wherein R¹ is substituted phenyl and R² is lower alkyl.

10. The compound as defined in claim 1 wherein one of R¹ and R² is phenyl substituted with halo or lower alkyl.

11. The compound as defined in claim 10 wherein the substituent on the phenyl is in the o-, m- or p-position.

12. The compound as defined in claim 1 having the name (S)-4-[[[1-(4-fluorophenyl)-3-(1-methylethyl)-indolizin-2-yl]ethynyl]hydroxyphosphinyl]-3-hydroxybutanoic acid, or esters or salts thereof; (S)-4-[[[3-(4-fluorophenyl)-1-(1-methylethyl)-2-indolizinyl]ethynyl]-hydroxyphosphinyl]-3hydroxybutanoic acid, or esters or salts thereof; (S)-4-[[[1-(4-fluorophenyl)-5,6,7,8-tetrahydro-3-(1-methylethyl)indolizin-2-yl]ethynyl]hydroxyphosphinyl]-3-hydroxybutanoic acid, or esters or salts thereof; (S)-4-[[2-[1-(4-fluorophenyl)-5,6,7,8-tetrahydro-3-(1-methylethyl)-2-indolizinyl]ethyl]hydroxyphosphinyl]-3-hydroxybutanoic acid, or esters or salts thereof; (S)-4-[[2-[3-(4-fluorophenyl)-5,6,7,8-tetrahydro-1-(1-methylethyl)-2-indolizinyl]ethyl]hydroxyphosphinyl]-3-hydroxybutanoic acid, or esters or salts thereof, or (S)-4-[[[3-(4-fluorophenyl)-5,6,7,8-tetrahydro-1-(1-methylethyl)-2-indolizinyl]ethynyl]hydroxyphosphinyl]-3-hydroxybutanoic acid, or esters or salts thereof.

13. A hypocholesterolemic or hypolipemic composition comprising a compound as defined in claim 1 and a pharmaceutically acceptable carrier therefor.

14. A method of inhibiting cholesterol biosynthesis which comprises administering to a patient in need of such treatment an effective cholesterol biosynthesis inhibiting amount of a compound as defined in claim 1.

* * * * *

UNITED STATES PATENT AND TRADEMARK OFFICE
CERTIFICATE OF CORRECTION

PATENT NO.    :   5,025,000
DATED         :   June 18, 1991
INVENTOR(S)   :   Donald S. Karanewsky It is certified that error appears in the above-identified patent and that said Letters Patent is hereby corrected as shown below:

Column 18, line 20, please change "or -C=C-" to -- or -C≡C- --;

In the Claims:

Column 59, Claim 1, line 67, please change "-CH=CH-$_2$ or -CH$_2$-$_4$" to read -- $\text{-(CH=CH)}_2$ or $\text{-(CH}_2\text{)}_4$ --;

Column 59, Claim 1, first line under structure, please change "or -C=C-" to --or -C≡C- --.

Signed and Sealed this

Twelfth Day of January, 1993

*Attest:*

DOUGLAS B. COMER

*Attesting Officer*   Acting Commissioner of Patents and Trademarks